United States Patent [19]

Vice

[11] Patent Number: 5,589,472
[45] Date of Patent: Dec. 31, 1996

[54] DIINDOLO COMPOUNDS AND PHARMACEUTICAL COMPOSITIONS CONTAINING THEM

[76] Inventor: Susan F. Vice, 1144 Sawmill Rd., Mountainside, N.J. 07092

[21] Appl. No.: 397,205
[22] PCT Filed: Sep. 9, 1993
[86] PCT No.: PCT/US93/08276
    § 371 Date: Mar. 10, 1995
    § 102(e) Date: Mar. 10, 1995
[87] PCT Pub. No.: WO94/07895
    PCT Pub. Date: Apr. 14, 1994

Related U.S. Application Data

[63] Continuation-in-part of Ser. No. 951,052, Sep. 25, 1992, abandoned.
[51] Int. Cl.⁶ .................... C07D 498/22; A61K 31/55; A61K 31/38
[52] U.S. Cl. .................... 514/183; 540/545; 540/546
[58] Field of Search ............... 540/450, 484, 540/545, 546; 514/183

[56] References Cited

FOREIGN PATENT DOCUMENTS 0410389  3/1991  European Pat. Off. .
0508792  4/1992  European Pat. Off. .

OTHER PUBLICATIONS

Liebigs Annalen Derchemie, No. 6, 1976 Weinhem pp. 1090–1102.
Fabre et al. Biorganic letters, vol. 2, No. 4, pp. 449–452, 1992.
5th Symposium Blackbury VA, Oct. 2, 1992.
Weinreb et al, Heterocycles, vol. 21, No. 1, 1984 pp. 309–316, 324.

*Primary Examiner*—Mukund J. Shah
*Assistant Examiner*—Pavanaram K. Sripada
*Attorney, Agent, or Firm*—Matthew Boxer; John J. Maitner

[57] ABSTRACT

The invention relates to compounds of the formula

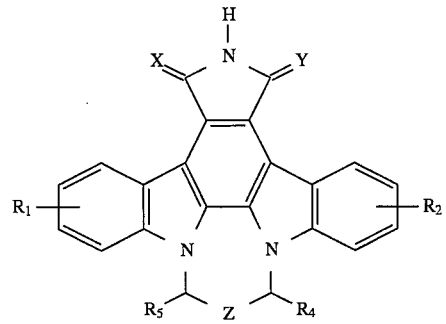

wherein X, Y, Z, $R_1$, $R_2$, $R_4$, and $R_5$, are as described herein. These compounds are useful as agents for the treatment of inflammation, tumors and psoriasis.

17 Claims, No Drawings

DIINDOLO COMPOUNDS AND PHARMACEUTICAL COMPOSITIONS CONTAINING THEM

This application is a 371 of PCT/US93/08276 Sep. 9, 1993, which is a CIP of U.S. application Ser. No. 07/951,052 filed Sep. 25, 1992, now abandoned.

SUMMARY OF THE INVENTION

The invention relates to compounds of the formula

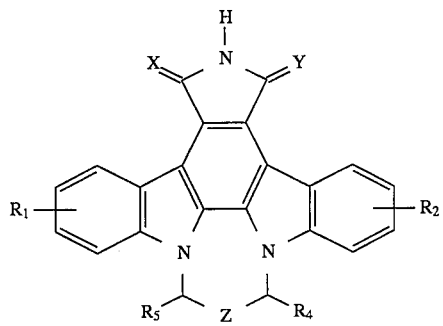

I or pharmaceutically acceptable salts thereof, wherein

X and Y are independently =O, =NH, (H,H) or (H,OH);

$R_1$ and $R_2$, are independently —H, —OH, —Cl, —F, —$OCH_3$, or —$CH_3$;

Z is N—$R_3$, O,

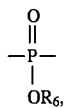

S, SO, or $SO_2$:

$R_3$ is —H, —OH, —$NH_2$, —$C_1$-$C_{10}$ alkyl,

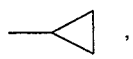,

—$CH_2Ph$, —Ar, heteroaromatic, —$(CH_2)_nCO_2H$, —$(CH_2)_2OH$, —$CH(CH_2OH)_2$, —$C(CH_2OH)_3$, —$CH_2CH(N(CH_3)_2)$, —$CH_2CH_2NH_2$, —$NHCH_3$, aralkyl, —$N(CH_3)_2$;

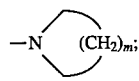

—$CH_2CH_2SH$, $CH_2CH_2SCH_3$, —$CH_2CO_2CH_3$, —$CH_2CO_2CH_2CH_3$, —$CH_2CN$; —$CH_2CH_2N_3$ and

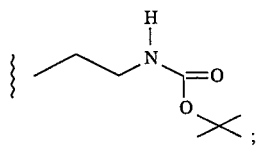;

n is 1 or 2;

m is 0, 1, 2 or 3;

$R_4$ and $R_5$ are the same or different and each independently is selected from the group consisting of H, —$(CH_2)_pOH$, —$(CH_2)_qNH_2$, —$(CH_2)_rNHCH_3$, —$(CH_2)_sN(CH_3)_2$, —$(CH_2)_tOCH_3$, —$(CH_2)_uCO_2CH_3$, —$CH_2CO_2CH_2CH_3$, —$CH_2CH_2CO_2CH_3$, —$CH_2CH_2CO_2CH_2CH_3$, —$CH_2CH_2CO_2$tert-Bu., —$CH_2CO_2$tert-Bu., —$CH_2CH_2CO_2$t Bu., and —$(CH_2)_vCO_2H$ —$(CH_2)_wCONH_2$;

$R_6$ is —$C_1$-$C_4$ alkyl;

p, q, r, s, t, u, v and w are each independently 1 or 2;

with the proviso that when Z is N—$R_3$, O,

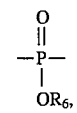

S, or SO, $R_4$ and $R_5$ are both H.

Preferred are compounds of formula I wherein Z is N—$R_3$. Among these are preferred compounds wherein $R_3$ is aralkyl, or especially —$(CH_2)_nCO_2H$, —$(CH_2)_2OH$, —$CH_2CH_2N(CH_3)_2$, —$CH_2CH_2SH$, —$CH_2CH_2SCH_3$, —$CH_2CO_2CH_3$, —$CH_2CO_2CH_2CH_3$, or —$CH_2CN$. Also preferred are compounds of formula I wherein $R_3$ is —H, —OH or —$CH_3$. Also preferred are compounds of formula I wherein $R_3$ is —$CH_2CH_2N(CH_3)_2$. Also preferred are compounds of formula I wherein Z is N—$R_3$, X and Y are both O and $R_3$ is —$CH_2CH_2OH$.

Also preferred are compounds of formula I wherein Z is S. Among these compounds wherein only one of X and Y is O, are especially preferred.

Also preferred are compounds of formula I wherein Z is SO.

Also preferred are compounds of formula I wherein Z is $SO_2$.

Also preferred are compounds of formula I wherein Z is O.

Also preferred are compounds of formula I wherein X and Y are both O.

Also preferred are compounds of formula I wherein $R_1$ and $R_2$ are both H.

Also preferred are compounds of formula I wherein Z is $SO_2$ and $R_4$ and $R_5$ are both H.

Exemplary of compounds of formula I of the invention are:

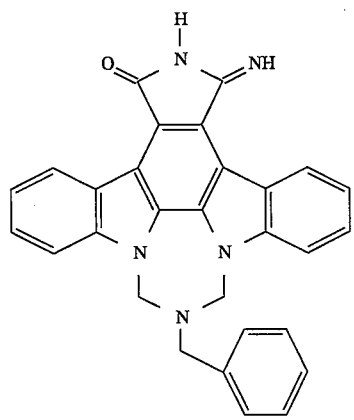

1.

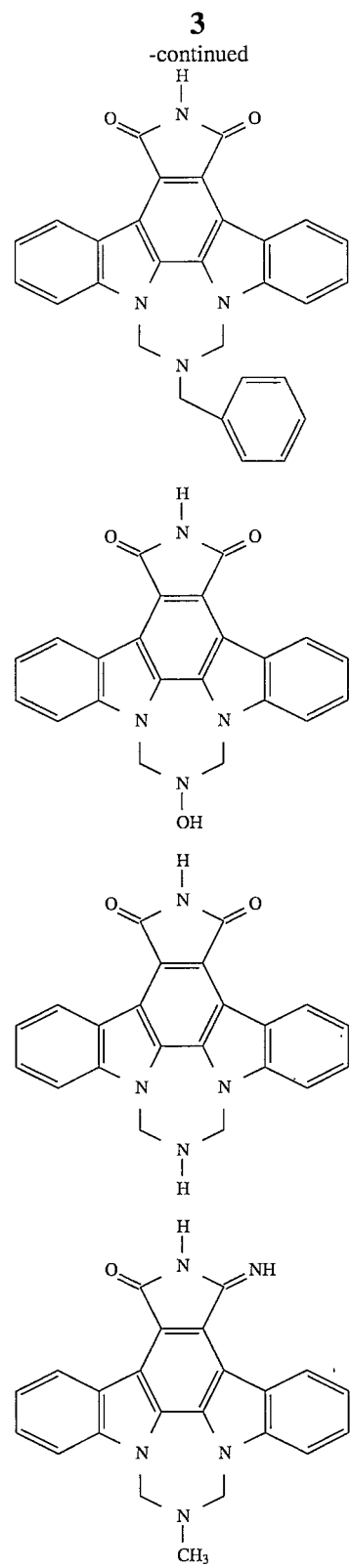
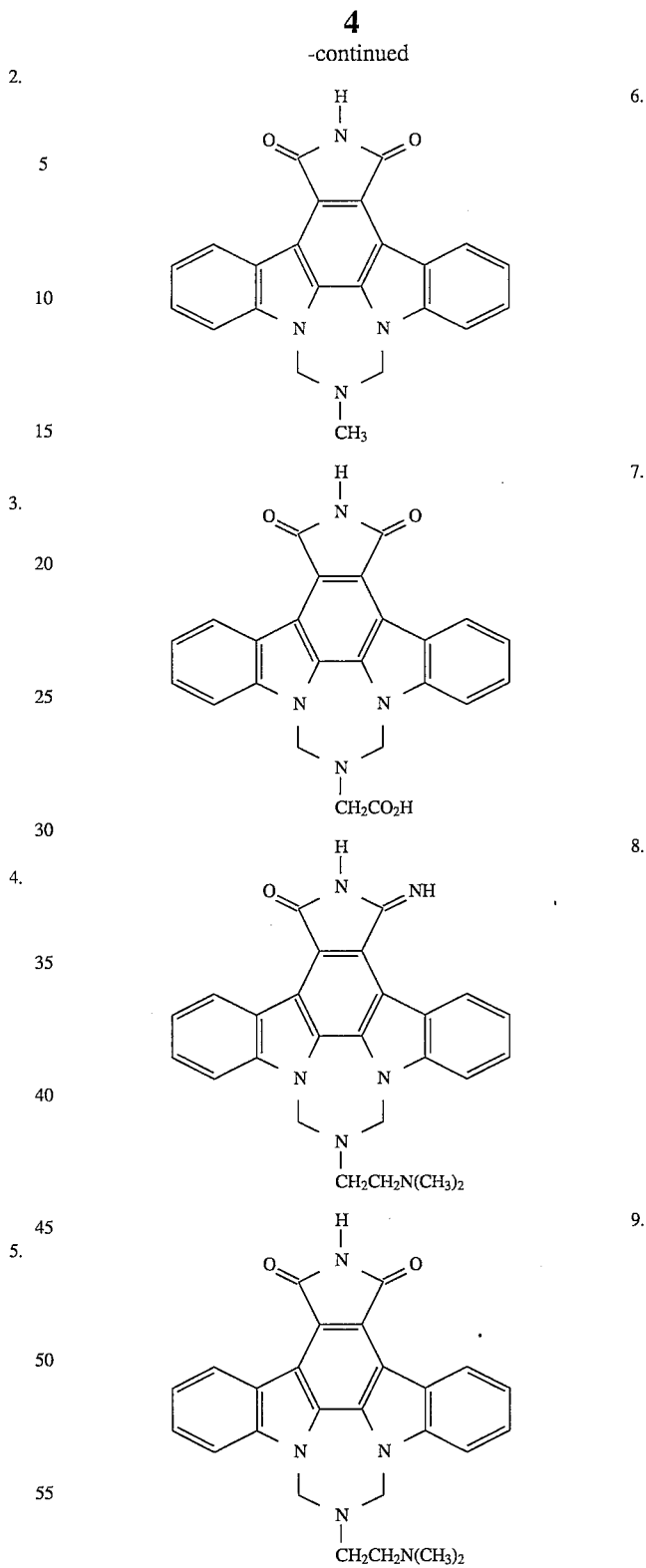

5
-continued
10.
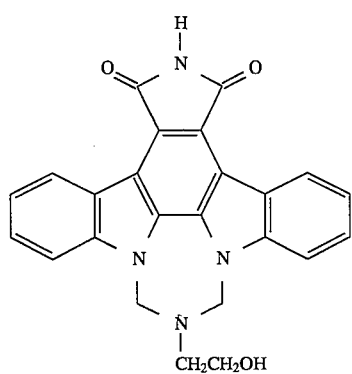
11.
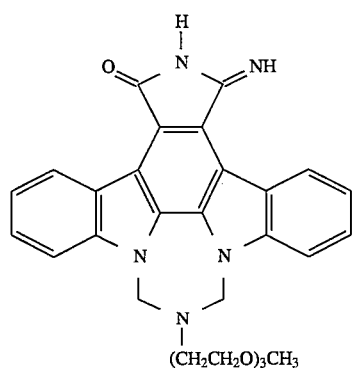
12.
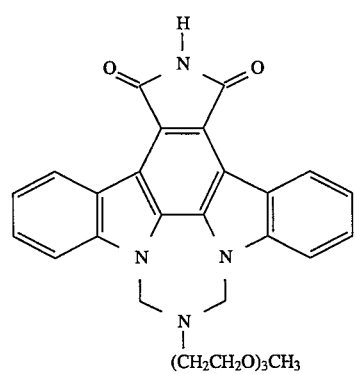
13.
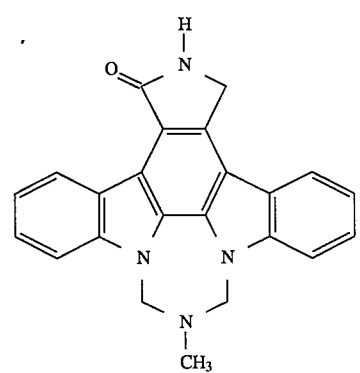
6
-continued
14.
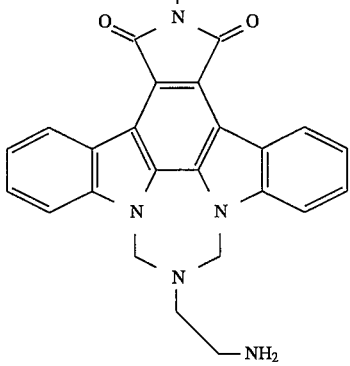
15.
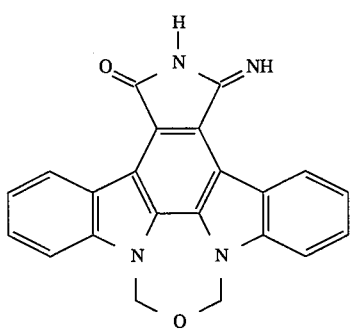
16.
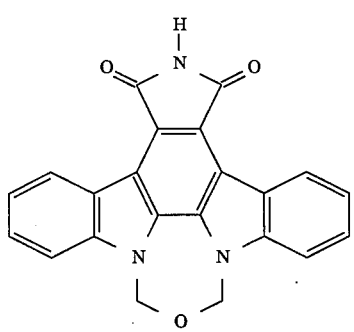
17.
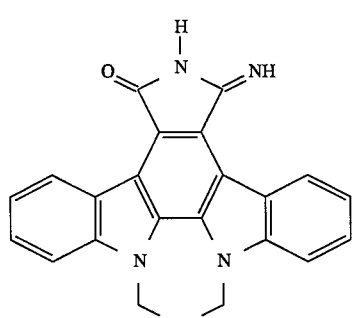
18.
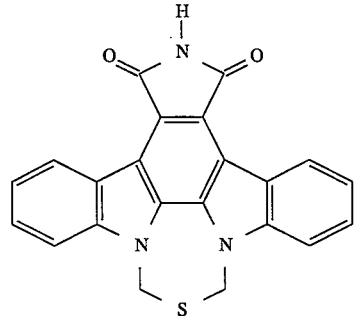

19. 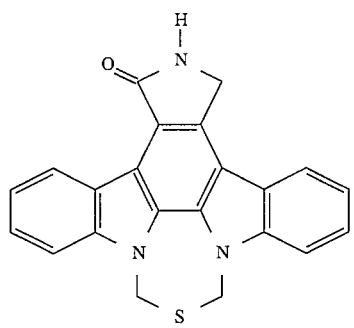

20. 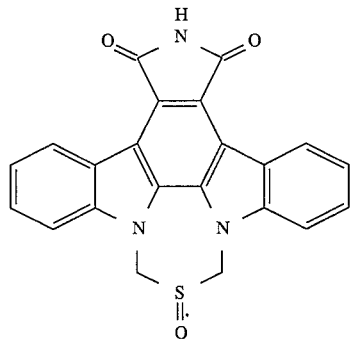

21. 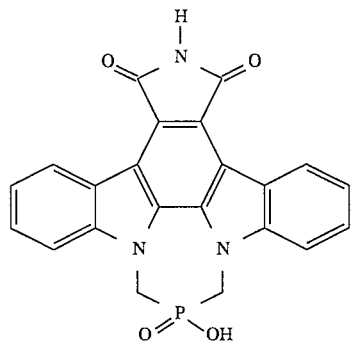

22. 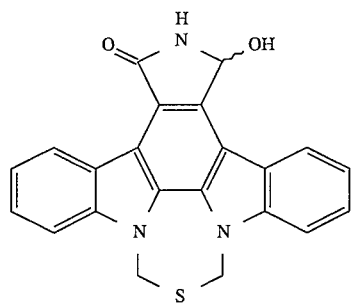

23. 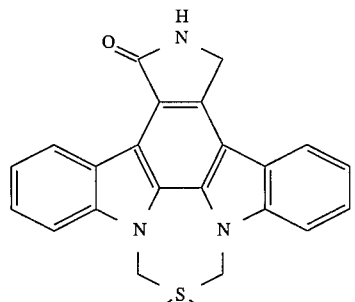

24. 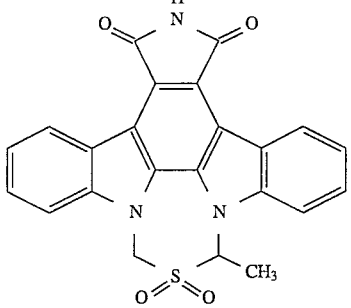

25. 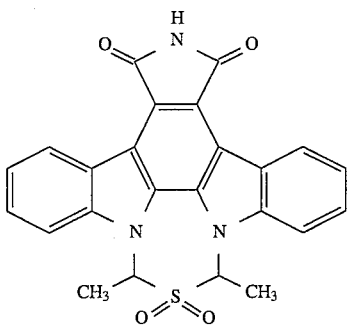

and

26. 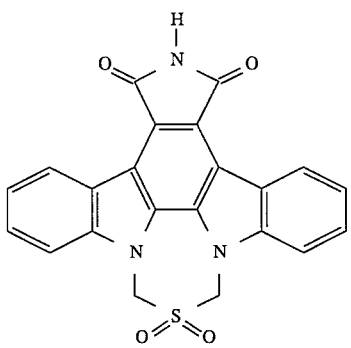

The most preferred compound of the invention is:

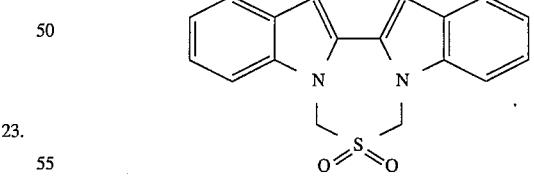

The invention also relates to a pharmaceutical composition comprising a therapeutically effective amount of a compound of formula I in combination with a pharmaceutically acceptable carrier.

The invention relates to a method of treating inflammation which comprises administering to a mammal in need of such treatment an anti-inflammatory effective amount of a compound of formula I for such purpose.

The invention also relates to a method of treating tumors which comprises administering to a mammal in need of such treatment an anti-tumor effective amount of a compound of formula I for such purpose.

The invention also relates to a method for treating psoriasis which comprises administering to a mammal in need of such treatment an anti-psoriatically effective amount of a compound of formula I for such purpose.

The invention also relates to a method for synthesizing compounds of formula I of the invention.

DETAILED DESCRIPTION OF THE INVENTION

The compounds of formula I can exist in unsolvated as well as solvated forms, including hydrated forms, e.g. the hemihydrate. In general, the solvated forms, with pharmaceutically acceptable solvents such as water, ethanol, and the like are equivalent to the unsolvated forms for the purposes of the invention.

Certain compounds of the invention can exist in stereoisomeric form. All such isomeric forms and mixtures thereof are within the scope of the present invention. Unless otherwise indicated, the methods of preparation disclosed herein may result in product distributions Which include all possible structural isomers, although it is understood that physiological response may vary according to stereochemical structure. The isomers may be separated by conventional means such as fractional crystallization or HPLC (high performance liquid chromatography).

The compounds of formula I form pharmaceutically acceptable salts. The preferred pharmaceutically acceptable salts are nontoxic acid addition salts formed by adding to a suitable compound of the invention about a stoichiometric amount of a mineral acid, such as HCl, HBr, $H_2SO_4$ or $H_3PO_4$ or of an organic acid such as acetic, propionic, valeric, oleic, palmitic, stearic, lauric, benzoic, lactic, para-toluenesulfonic, methane sulfonic, citric, maleic, fumaric, succinic and the like, respectively.

When utilized herein and in the appended claims, the following terms, unless otherwise specified have the following meanings "alkyl"—(including the alkyl portions of alkoxy, etc) represents a straight or branched, saturated hydrocarbon chain having from 1 to 10 carbon atoms. The number of carbon atoms may be designated. For example, "$C_1$-$C_3$ alkyl" represents a straight or branched, saturated hydrocarbon having from 1 to 3 carbon atoms. For example, "$C_7H_{13}$" represents all straight or branched, saturated hydrocarbon having 7 carbon atoms. Examples of alkyl groups are n-heptyl, ethyl, n-propyl, 1-methyl ethyl, cyclopropyl, n-butyl, 1-methyl propyl, 2-methyl propyl, tert-butyl, n-pentyl, 1-methyl butyl, 1,1-dimethyl propyl, 2,2-dimethyl propyl, 1,2-dimethyl propyl, 1-ethyl propyl, n-hexyl, 1-methyl pentyl, 2-methyl pentyl, 3-methyl pentyl, 4-methyl pentyl, 1,1-dimethyl butyl, 2,2-dimethyl butyl, 3,3-dimethyl butyl, 1,2-dimethyl butyl, 1,3-dimethyl butyl, 2,3-dimethyl butyl, 1-ethyl butyl, 2-ethyl butyl, 1,1,2-trimethyl propyl, 1-ethyl-1-methyl propyl, 2-propene, 1-methyl hexyl, 2-methyl hexyl, 3-methyl hexyl, 4-methyl hexyl, 5-methyl hexyl, 1,2-dimethyl pentyl, 1,3-dimethyl pentyl, 1,4-dimethyl pentyl, $C_7H_{15}$, $C_8H_{17}$, $C_9H_{19}$, $C_{10}H_{21}$, and cyclohexyl.

"acyl"—represents a CO-alkyl, a CO-substituted alkyl, a CO-aryl or a CO-aralkyl wherein alkyl, substituted alkyl, aryl and aralkyl are as defined herein.

"aryl"—represents a mono or bi-cyclic aromatic system or heteroaromatic system. Examples of preferred aryl groups include those having from 6 to 14 carbon atoms. Representative examples include phenyl, 1-naphthyl, 2-naphthyl, and quinolinyl. The aryl group may contain additional substituents selected from the group consisting of: halogen atoms (e.g., Cl, Br, F, and/or I), alkoxy, alkyl, and amino.

"aralkyl"—represents an alkyl group as defined above in which an aryl group as defined above replaces one of the alkyl hydrogen atoms. Representative examples include —$CH_2$-phenyl, —$CH_2CH_2$phenyl, 4-hydroxybenzyl, 4-t-butyldimethylsilyloxybenzyl, and the like.

In the formula schemes below, the following abbreviations are used.

As used herein

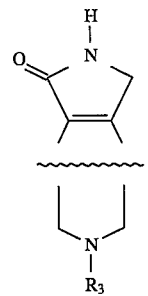

is an abbreviation for the compound

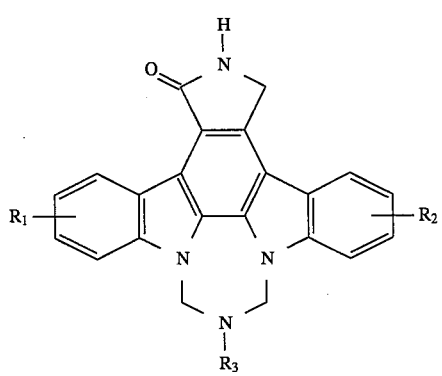

11
-continued
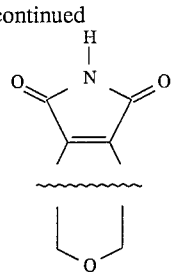
Similarly, 
is an abbreviation for the compound
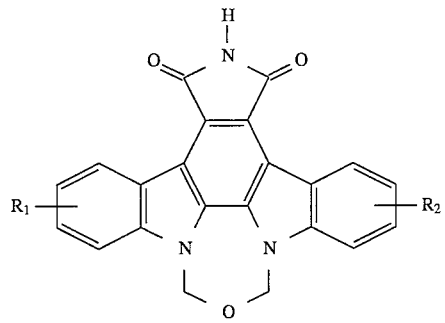
Similarly, 
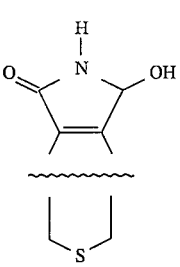
12
is an abbreviation for the compound
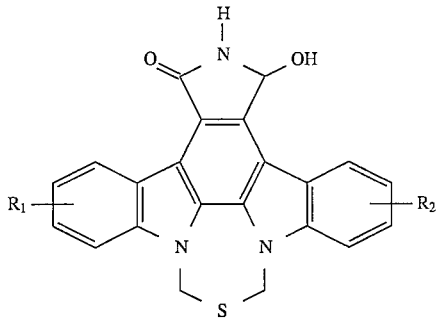
The compounds of formula I wherein Z is $N-R_3$ may be prepared by the methods described below with reference to Formula Scheme 1 wherein $R_1$, $R_2$, and $R_3$ are as described above unless designated otherwise.
FORMULA SCHEME 1
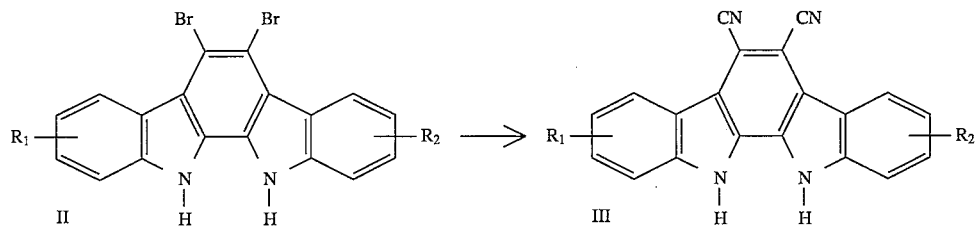

-continued
FORMULA SCHEME 1

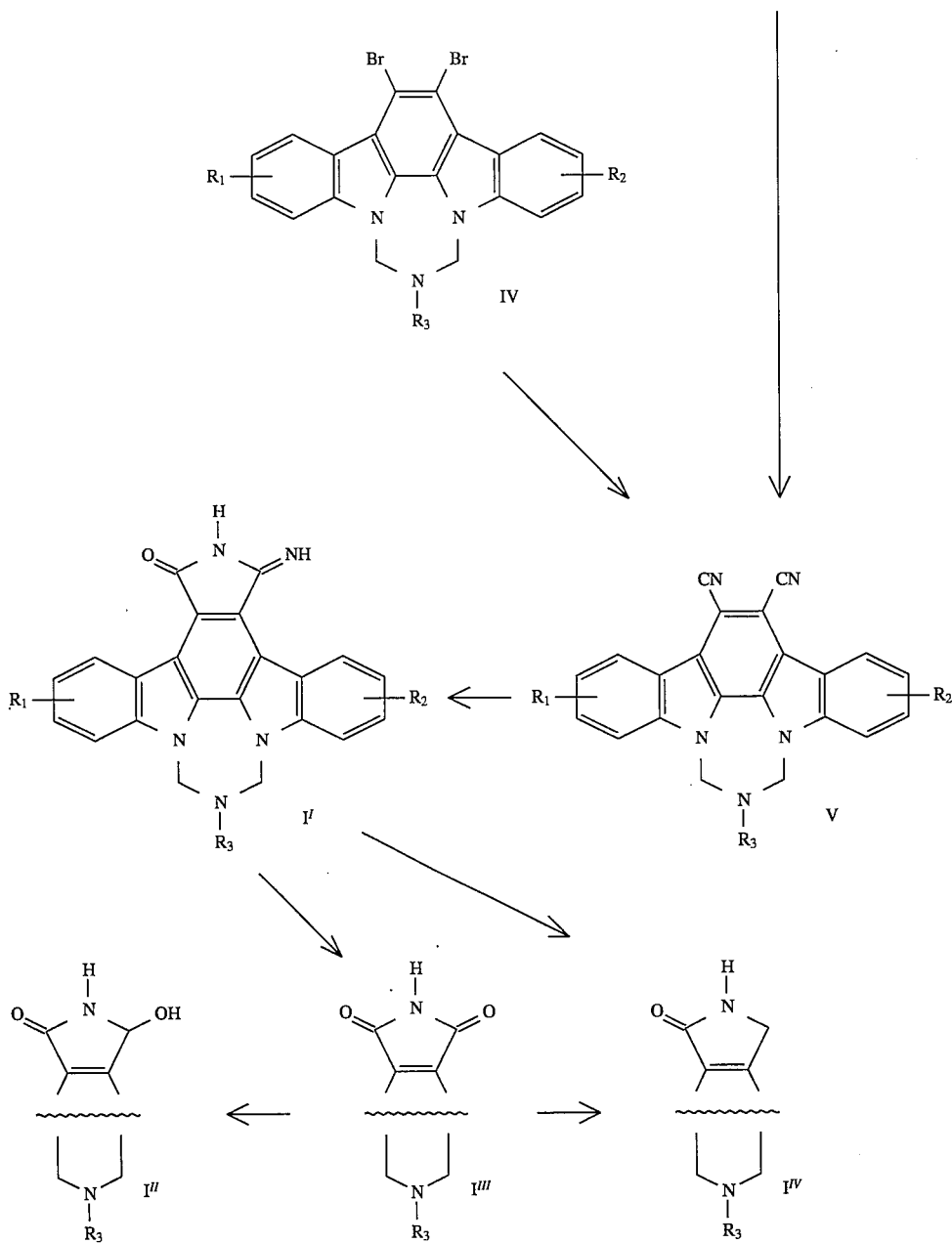

wherein $R_1$, $R_2$, and $R_3$ are as described herein.

It will be understood by one skilled in the art that where $R_3$, in the scheme above, is —$NH_2$, —$NHCH_3$, or —$CH_2CH_2NH_2$, that preparation of a compound of formula I will require the use of a protecting group, such as benzyl.

It will be understood that compounds of formulas $I^I$, $I^{II}$, $I^{III}$, and $I^{IV}$ are encompassed by formula I.

Compounds of formula II may be prepared by known methods from compounds whose preparation is described in the six just above mentioned publications.

Unless otherwise indicated the reactions below are run under an inert atmosphere such as argon or nitrogen.

Unless otherwise indicated, degrees or "°" means degrees Celsius throughout the specification.

As shown in Formula Scheme 1 above, a compound of formula II may be reacted with two to 100 equivalents of formalin, which is (37%) aqueous formaldehyde, preferably two equivalents, and about one equivalent to about 100 equivalents of a primary amine of the formula $HNR_3$ wherein $R_3$ is as described above. More preferably about 1 equivalent of $HNR_3$ is employed. Alternatively, hydroxylamine may be used in a polar and water soluble solvent such as ethanol, tetrahydrofuran (THF), water or acetic acid and the reaction may be run at a temperature from about 5° to about 100° C., more preferably at room temperature to obtain a compound of formula IV.

A compound of formula IV may be isolated by conventional means such as filtration or it may be used in the next step of the synthesis without purification. In the next step of the synthesis a compound of formula IV is reacted in a nitrile forming reaction; that is, with CuCN and optionally in the presence of NaI. The solvent for the reaction may be dimethylacetamide or dimethylformamide (DMF). The reaction is run at temperatures in the range of about 100° to about 210° C., more preferably at about 190° C. to obtain a compound of formula V.

A compound of formula V may be isolated by conventional means such as filtration, or it may be cyclized directly by reaction with a nucleophilic reagent such as NaOH or NaOCH$_3$ more preferably KOH/H$_2$O in DMSO at temperatures in the range of about 0° to about 120° C., more preferably at about 100° C. to obtain a compound of formula I$'$.

A compound of formula I$'$ may be isolated by conventional means such as filtration, or it may be reacted with an aqueous acidic reagent such as HCl, H$_2$SO$_4$ or more preferably, trifluoroacetic acid (TFA) in DMSO and H$_2$O at temperatures in the range of about 10° to about 100° C., more preferably at about 25° C. to obtain a compound of formula I$'''$. This compound may be isolated by methods conventional in the art such as chromatography or crystallization.

Alternatively, a compound of formula I$'$ may have its imine portion removed by reaction with a reducing reagent such as BH$_3$ or more preferably NaCNBH$_3$ in an acidic solvent such as glacial acetic acid at a temperature in a range of about 25° C. to 100° C., preferably 60° C. for a period of about 1 hour to about 24 hours, preferably about 1 hour, to obtain a compound of formula I$^{IV}$ which may be isolated by conventional means such as chromatography, crystallization or, more preferably, precipitation.

A compound of formula I$'''$ may be reacted with a reducing agent such as DIBAL, or more preferably lithium aluminum hydride (LiAlH$_4$) in a polar organic solvent such as dichloromethane at a temperature in the range of about −20° C. to about 27° C. in an atmosphere of nitrogen or argon. The resulting alcohol of formula I$''$ may be isolated by conventional means such as precipitation, crystallization, or more preferably chromatography.

A compound of formula I$'''$ may be reacted with a reducing agent such as LiBH$_4$, or more preferably NaBH$_4$ in the presence of boron trifluoride etherate and diglyme at a temperature of about −10° C. to about 30° C. preferably about 0° C., for about 3 to about 18 hours. The resulting compound of formula I$^{IV}$ can be isolated by conventional means such as precipitation.

A similar reduction is carried out in other formula schemes of the invention. Specifically, in Formula Scheme 2 a compound of formula I$^{VII}$ is converted to a compound of formula I$^{VI}$ using a similar reduction.

Alternatively, a compound of formula II may be reacted with a nitrile forming reagent such as CuCN in the presence of a salt such as lithium iodide, KI, or more preferably, NaI in a polar, organic solvent such as DMF, or more preferably, N,N-dimethylacetamide (DMAC), at a temperature in the range of about 100° C. to about 210° C., more preferably at about 190° C. for about 2 to about 8 hours. After a conventional workup, a compound of formula III may be isolated by standard means such as crystallization, or precipitation.

A compound of formula III may be directly converted to a compound of formula V by a reaction analogous to the conversion of a compound of formula II to a compound of formula IV in Formula Scheme 1.

Compounds of formula I of the invention can be formed directly using Arcyriaflavin A and derivatives thereof, that is

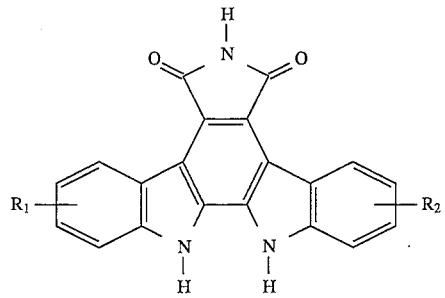

wherein R$_1$ and R$_2$ are as described herein.

*Tetrahedron*, Vol. 44, No. 10, pp.2887 to 2892 (1988), is herein incorporated by reference. J. Org. Chem., 1989, 54, pages 824–828, which is herein incorporated by reference, describes the preparation of Arcyriaflavin A and these derivatives of it. Using these compounds as starting materials and the appropriate reaction conditions given in Formula Scheme 1 above a compound of formulas I$''$, I$'''$, and I$^{IV}$ can be obtained. For example, a compound of formula I$''$ could be prepared analogously to the reactions of compounds of formulas II→IV→V→I$'$→I$'''$→I$''$. The compound

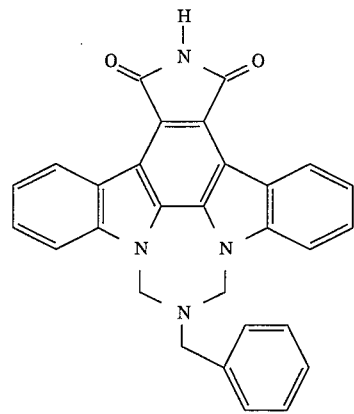

was prepared analogously to the reactions of compounds of formulas II→IV→V→I$'$→I$'''$.

More preferred is the reaction of dibromo or dicyano indolocarbazole as shown in Formula Scheme 1 above.

Most preferred are the reactions wherein a protecting group such as triisopropyl silyl is used as shown in Formula Scheme 4 below.

Compounds of formula I wherein Z is O can be prepared as shown in Formula Scheme 2 below.

FORMULA SCHEME 2

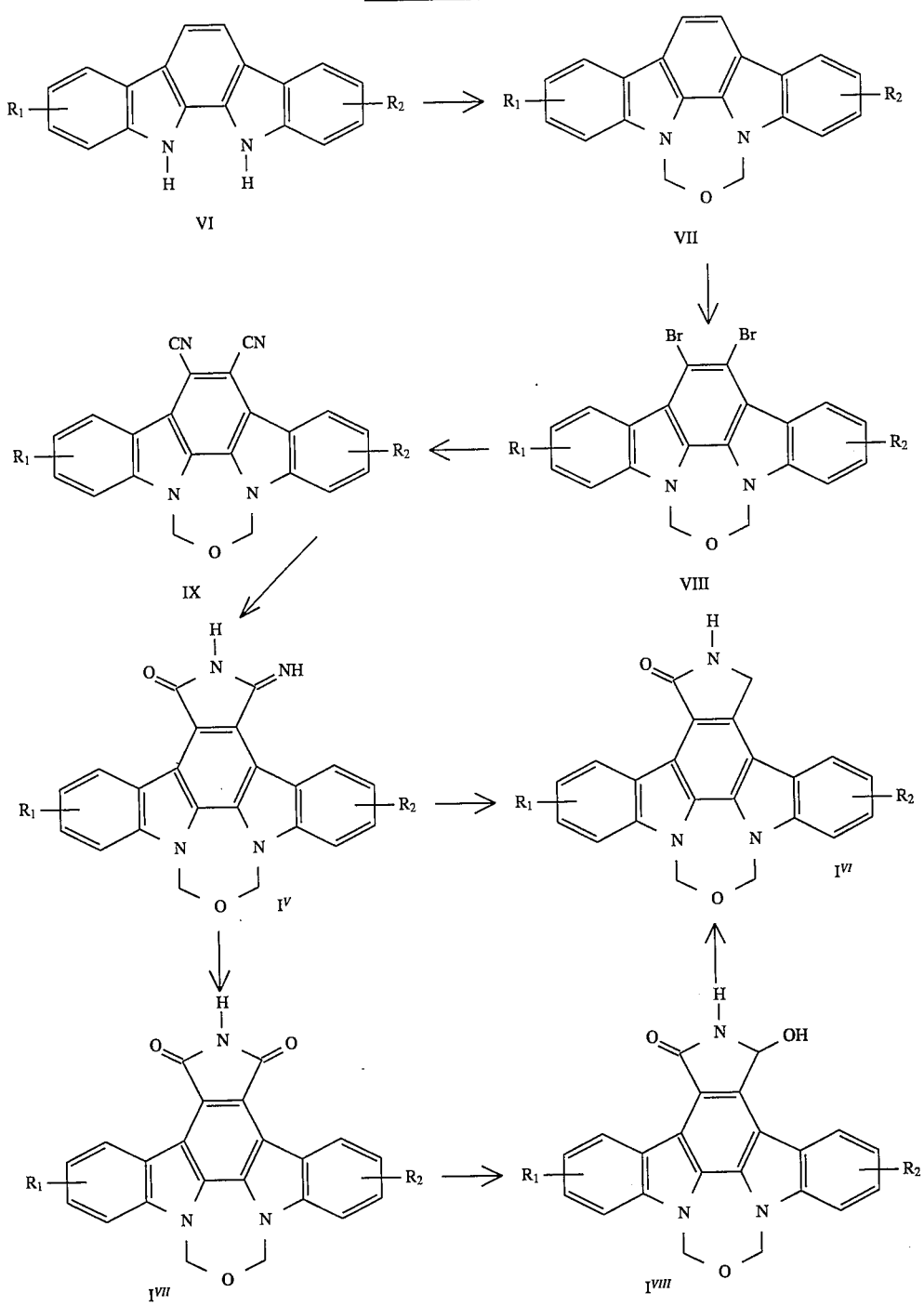

wherein $R_1$, and $R_2$ are as described herein.

The compound of formula VI is known or can be prepared in accordance with known methods. For example, it may be prepared by methods set forth in Bhide et al Chem and Ind., 1957, 363; Mann and Wilcox J. Chem Soc., 1958, 1525; Moldenhauser and Simon, Chem. Bericht, 1969, 102, 1198; Bergman and Pelcman, Tet. Letts., 1987, 28, 4441; Bergman, Chemica Scripta, 1987, 27, 539; and Bergman and Pelcman, J. O. C., 1989, 54, 824. These six publications that have just been mentioned are hereby incorporated by reference.

As shown in Formula Scheme 2 above, the compound of formula VI may be reacted with bis(chloromethyl)ether in a polar organic solvent such as dichloromethane, toluene, or more preferably tetrahydrofuran (THF). A phase transfer catalyst such as $nBu_4NHSO_4, nBu_4NBr$ or more preferably Aliquat® 336 is added. The mixture is made basic with an aqueous base such as KOH or more preferably NaOH. After stirring for a half hour to an hour, additional bis(chloromethyl)ether is added. The reaction is further stirred vigorously for an additional hour or two. After workup by conventional means, and purification which can be, for example, by crystallization, the compound of formula VII may be obtained.

A compound of formula VII may be reacted with a brominating reagent such as $Br_2$, $Ph(CH_3)_3NBr.Br_2$, or more preferably, N-bromosuccinimide in a polar, organic solvent such as dimethylformamide or dichloromethane under an inert atmosphere such as argon or nitrogen at a temperature in the range of about 0° to about 60° C. for about 1 to about 4 hours to obtain a compound of formula VIII.

A compound of formula VIII can be converted to a compound of formula IX using reaction conditions analogous to those set forth in the conversion of compounds of formula IV to compounds of formula V in Formula Scheme 1 above.

A compound of formula IX can be converted to a compound of formula $I^V$ using reaction conditions analogous to those set forth in the conversion of compounds of formula V to compounds of formula $I'$ in Formula Scheme 1 above.

A compound of formula $I^V$ can be converted to a compound of formula $I^{VI}$ using reaction conditions analogous to those set forth in the conversion of compounds of formula $I'$ to compounds of formula $I^{IV}$ in Formula Scheme 1 above.

A compound of formula $I^V$ can also be converted to a compound of formula $I^{VII}$ using reaction conditions analogous to those set forth in the conversion of compounds of formula $I'$ to compounds of formula $I'''$ in Formula Scheme 1 above.

A compound of formula $I^{VII}$ can be converted to a compound of formula $I^{VIII}$ using reaction conditions analogous to those set forth in the conversion of compounds of formula $I''''$ to compounds of formula $I''$ in Formula Scheme 1 above.

A compound of formula $I^{VIII}$ can be reacted with a reagent such as $BH_3$ in a polar organic solvent such as dichloromethane or more preferably, THF. The reaction is run at a temperature in the range of 20° C., to about 65° C. more preferably at about room temperature for a period of about 18 to about 36 hours, more preferably about 20 hours under an atmosphere of nitrogen to obtain a compound of formula $I^{VI}$. An analogous reaction can be run when Z is S, SO, $SO_2$. A compound of formula $I^{VI}$ may be isolated by conventional means such as precipitation, or more preferably, chromatography.

It will be understood that compounds of formulas $I^V$, $I^{VI}$, $I^{VII}$, and $I^{VIII}$ are encompassed by formula I.

Compounds of formula I wherein Z is S, SO, or $SO_2$ can be prepared as shown in Formula Scheme 3 below.

FORMULA SCHEME 3

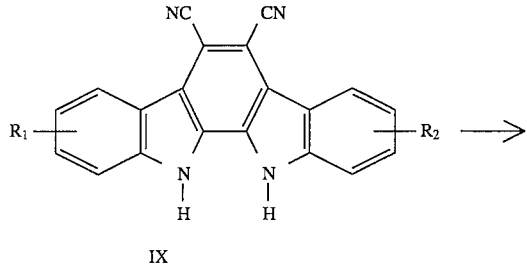

IX

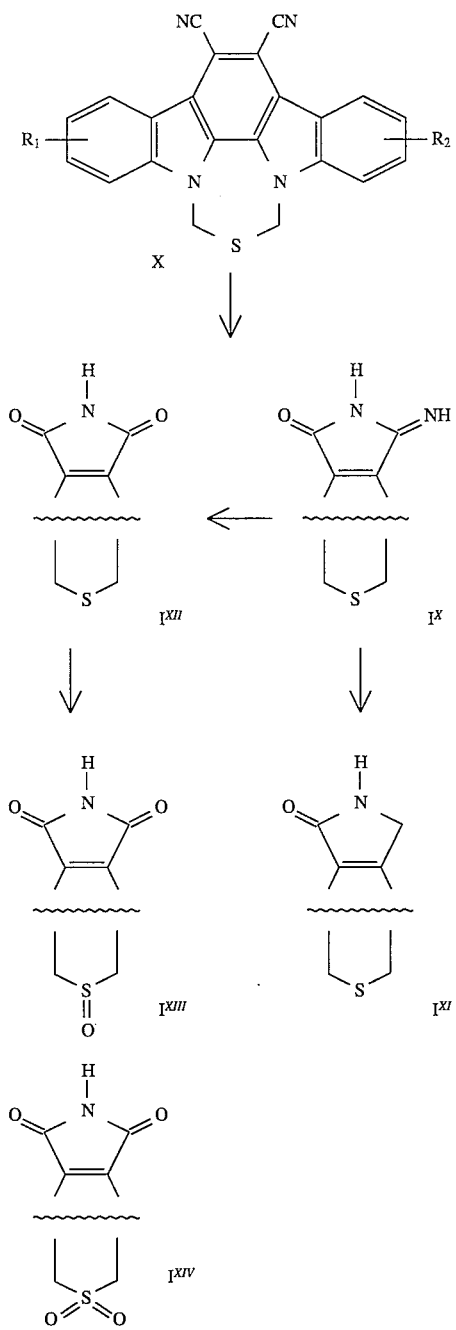

wherein $R_1$ and $R_2$ are as described herein.

A compound of formula IX may be converted to a compound of formula X by reaction with bischloromethyl sulfide in the presence of a strong base such as KH, LDA, or more preferably, sodium hydride in a polar aprotic, organic solvent such as THF, or more preferably, DMF under an atmosphere of argon or nitrogen. The bischloromethyl sulfide can be added dropwise. The mixture can be stirred for about 5 to about 25 hours, preferably about 20 hours. The reaction can be cooled down to −30° C. to about 10° C., preferably about 0° C.

The resulting compound of formula X may be isolated by conventional means such as chromatography or more preferably precipitation.

A compound of formula X may be converted to a compound of formula $I^X$ by a reaction analogous to that by which a compound of formula V is converted to a compound of formula $I'$ in Formula Scheme 1 above.

A compound of formula $I^X$ may be converted to a compound of formula $I^{XII}$ by a reaction analogous to that by which a compound of formula $I'$ is converted to a compound of formula $I^{III}$ in Formula Scheme 1 above.

A compound of formula $I^X$ may be converted to a compound of formula $I^{XI}$ by a reaction analogous to that by which a compound of formula $I'$ is converted to a compound of formula $I^{IV}$ in Formula Scheme 1 above.

A compound of formula $I^{XII}$ may be converted to a compound of formula $I^{XIII}$ by reaction with no more than about 0.6 equivalents of an oxidant such as sodium meta-periodate or peracetic acid or more preferably, meta-chloroperoxybenzoic acid (MCPBA) in a polar, aprotic organic solvent such as DMF or more preferably, dichloromethane at a temperature in the range of about −5° C. to about 25° C. more preferably, at about 0° C. The resulting compound of formula $I^{XIII}$ may be isolated by conventional means such as precipitation, or more preferably, chromatography.

A compound of formula $I^{XII}$ may be convened to a compound of formula $I^{XIV}$ by an oxidation analogous to that by which a compound of formula $I^{XII}$ is convened to a compound of formula $I^{XIII}$ as shown, just above except that more than 2.0 equivalents of the oxidant are employed. The preferred oxidant in this reaction is monoperoxyphthalic acid, magnesium salt hexahydrate.

FORMULA SCHEME 4

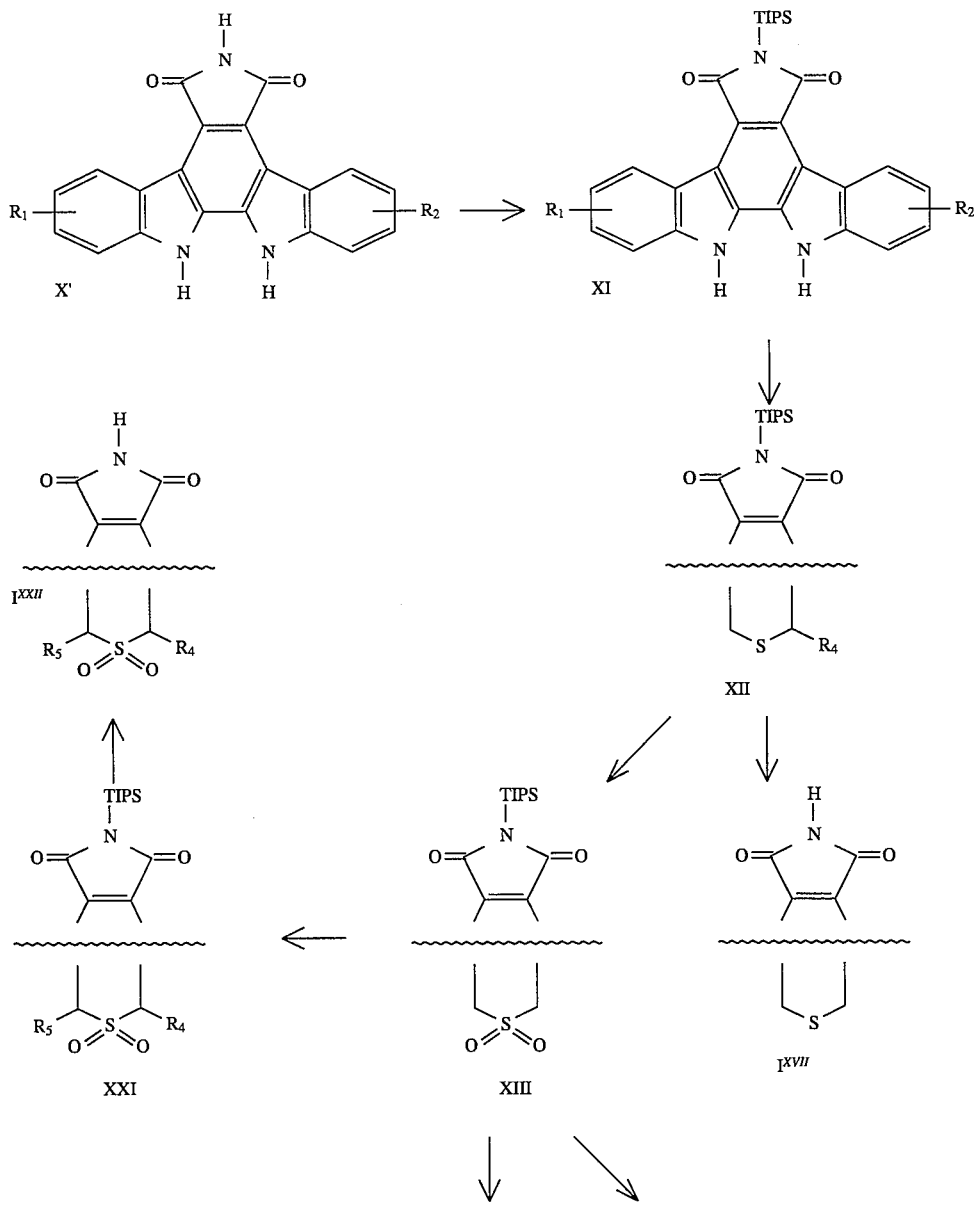

-continued
FORMULA SCHEME 4

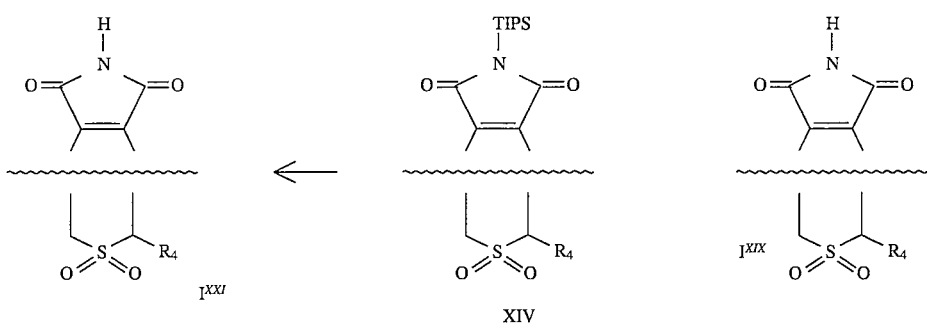

wherein $R_1$, $R_2$, $R_4$, and $R_5$ are as described herein and TIPS is triisopropylsilyl.

A compound of formula X' may be converted to a compound of formula XI, which is protected by the group, TIPS, by conventional means, or more preferably by treating a compound of formula X' with an amine base, preferably diisopropylethylamine and 0.2 to 5 equivalents, most preferaby 0.9 equivalents of an N,N-disubstituted trifluoroaceamide, in an organic solvent such as dichloromethane, more preferably THF, followed by the addition of 1 to 5 equivalents most preferably 1 equivalent of triisopropyl silyl trifluoromethane sulfonate (TIPSOTf). The resulting solution can be stirred for 30 minutes to 18 hours most preferably 6 hours, at 0° C. to 25° C., most preferably 25° C. The resulting compound of formula XI can be isolated by conventional means and purified by crystallization or, more preferably by chromatography.

A compound of formula XI may be converted to a compound of formula XII by a reaction analogous to that by which a compound of formula IX is converted to a compound of formula X as shown in Formula Scheme 3 above.

A compound of formula XII may be converted to a compound of formula XIII by an oxidation analogous to that by which a compound of formula $I^{XII}$ is converted to a compound of formula $I^{XIV}$ in Formula Scheme 3 above.

A compound of formula XIII may be converted to a compound of formula XIV by reaction with 1 to 10 equivalents of a basic reagent such as NaH, LDA, or more preferably sodium hexamethyldisilylamide $(Na(N-Si(CH_3)_3)_2)$ at a temperature in the range of about $-78°$ C. and 0° C., more preferably $-30°$ C., in an organic solvent such as diethyl ether, diglyme or more preferably THF. The resulting solution can be treated with an alkylating agent such as bromoethyl acetate or benzylchloro methyl ether, most preferably, methyl iodide at about $-78°$ to about 25° C., most preferably at about 0° C. The resulting compound of formula XIV can be isolated by conventional means such as precipitation or more preferably, chromatography.

A compound of formula XIII may be converted to a compound of formula XXI by a reaction analogous to that by which a compound of formula XIII is converted to a compound of formula XIV except that at least two equivalents of a basic reagent must be used.

Alternatively, a compound of formula XII may be converted to a compound of formula $I^{XVII}$ by treatment with a reagent such as cesium fluoride or more preferably tetra-n-butyl ammonium fluoride in an organic solvent such as dichloromethane, toluene, or more preferably THF. The resulting compound of formula $I^{XVII}$ can be isolated by conventional means.

A compound of formula XIII may be converted to a compound of formula $I^{XIX}$ by a reaction analogous to that by which a compound of formula XIV is converted to a compound of formula $I^{XXI}$ as shown in Formula Scheme 4 above and as described in examples 40 or 45.

The resulting compound of formula $I^{XIX}$ can be isolated by conventional means.

FORMULA SCHEME 5

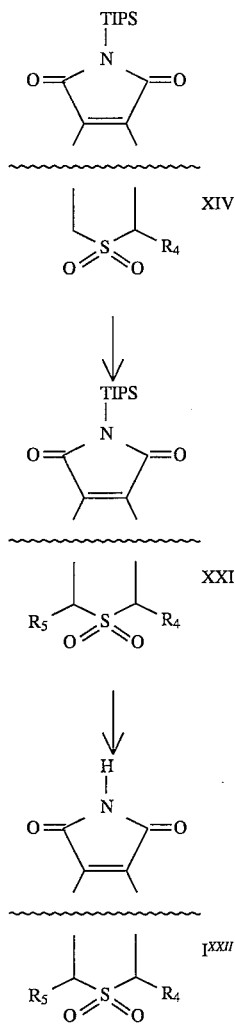

Note: TIPS=(triisopropyl)silyl

As shown in Formula Scheme 5 above, the compound of formula XIV, may be converted to a compound of formula XXI by reaction with 1 to 10 equivalents of a basic reagent such as NaH, LDA, or more preferably sodium hexamethyldisilylamide ($Na(NSi(CH_3)_3)_2$) at a temperature in the range of about $-78°$ C. and $0°$ C., more preferably $-30°$ C., in an organic solvent such as diethyl ether, diglyme or more preferably THF. The resulting solution can be treated with an alkylating agent such as bromoethyl acetate or benzyl chloromethyl ether, most preferably, methyl iodide at about $-78°$ to about $25°$ C., most preferably at about $0°$ C. The resulting compound of formula XXI can be isolated by conventional means such as chromatography.

A compound of formula XXI may be converted to a compound of formula $I^{XXII}$ in an analogous manner to the deprotection reaction described in Formula Scheme 4 above.

The preparation of the phosphorous compound of formula

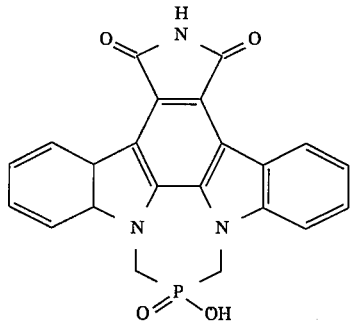

$I^{XXVIII}$ is described in examples 35, 36, and 37. Compounds of formula

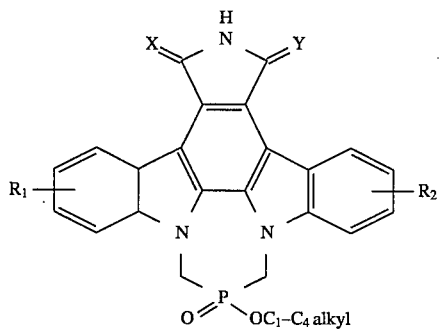

$I^{XXIII}$ of the invention can be prepared by treating the phosphinic acid compound of example 37 with a $C_1$-$C_4$ alkyl diazo compound such as diazo methane in an organic solvent such as diethyl ether or toluene, preferably THF, at room temperature. The resulting phosphinate can be isolated by evaporation of the solvent. Alternatively, the phosphinates can be made by treatment of the corresponding phosphinic acid with a $C_1$-$C_4$ alcohol in the presence of a catalyst such as $BF_3.OEt_2$, $H_2SO_4$ or preferably p-TSA.$H_2O$ at a temperature of between about $25°$ C. and the boiling point of the alcohol. The phosphinate can be isolated by crystallization or precipitation with water.

It will be understood that compounds of formulas $I'$, $I''$, $I^{III}$, $I^{IV}$, $I^V$, $I^{VI}$, $I^{VII}$, $I^{VIII}$, $I^X$, $I^{XI}$, $I^{XII}$, $I^{XIII}$, $I^{XIV}$, $I^{XVII}$, $I^{XIX}$, $I^{XXI}$, $I^{XXII}$, and $I^{XXIII}$ are encompassed by formula I.

It will be understood that the silicon alkyl protecting groups shown in the above reaction scheme may be replaced by other protecting groups known in the art such as tert-butyl dimethyl silyl, trimethylsilylethoxymethyl or benzyloxymethyl.

PKC has been implicated in many signal transduction processes. The PKC inhibitors outlined above are useful in the treatment of inflammatory diseases such as psoriasis and can also be used as therapeutic agents in the treatment of mammalian tumors.

The potential for compounds of formula I of the invention to have anti-tumor activity, may be demonstrated by their ability to inhibit protein Kinase C ("PKC") in vitro as shown in the test protocol just below.

Test Methods

A. Protein Kinase C ("PKC") Protocol

Protein Kinase C (PKC) was partially purified from rat brain by chromatography on DEAE-Sephacel according to Shearman et al, Methods in Enzymology 1658:347–351 (1989) and Bishop et al, Biochemical Pharmacology 40:2129–2135 (1990) which are hereby incorporated by reference. PKC was assayed in a reaction mixture (0.25 mL total volume) containing: 20 mM Tris-HCl (pH 7.5); 200 µg/mL histone III-S 10 mM $MgCl_2$; 5 µM [$\gamma$-$^{32}$] ATP ($4\times10^6$ cpm/nmol); 200 µM $CaCl_2$; 32 µg/mL phosphatidylserine; 1.6 µg/mL 1-oleoyl-2-acetyl glycerol and various concentrations of compounds of formula I of the invention were added from stock solutions in dimethylsulfoxide (DMSO). The final concentration of DMSO in the reaction was 2%. Reactions were started by addition of approximately 7 µg of partially purified PKC and allowed to proceed at $23°$ C. for 15 minutes. Reactions were terminated by addition of 1 mL of ice-cold 15% trichloracetic acid and 1 mL of cold 0.5 mg/mL bovine serum albumin to precipitate the histone III-S substrate. After 10 minutes on ice, precipitated phosphoproteins were collected on Whatman GF/C filters using a Brandel cell harvester. Filters were placed in scintillation vials with 5 mL of Ready Safe scintillation cocktail and radioactivity trapped on the filter was quantitated by liquid scintillation counting. Percent inhibition of PKC activity was calculated relative to the activity observed in the DMSO controls.

The following data demonstrate the activity of the compounds of the invention in the above protocol.

TABLE I

IN VITRO INHIBITION OF PKC

| COMPOUND NO. | $IC_{50}$ (nanomolar) except where otherwise indicated |
|---|---|
| 1 | >5 µM |
| 2 | >50 µM |
| 3 | 90 |
| 4 | 145 |
| 5 | 150 |
| 6 | 86 |
| 7 | 480 |
| 8 | 160 |
| 9 | 120 |
| 10 | 17 |
| 11 | ~500 |
| 12 | ~100 |
| 13 | 90 |
| 14 | not tested |
| 15 | 62 |
| 16 | 11 |
| 17 | 24 |
| 18 | 14 |
| 26 | 2.0 |
| trans-25 | 120 |
| cis-25 | 2.4 |
| 19 | 7.0 |
| 20 | 19.0 |
| 21 | not tested |
| 22 | not tested |
| 23 | 5.0 |
| 24 | not tested |

As is shown in the table above, the cis and trans forms of compound 25 were tested separately for biological activity.

Tumor Cell Invasion Assay

The cell invasion assay quantitates the ability of malignant cells to invade a reconstituted basement membrane matrix. The assay is performed essentially as described in the two articles which are cited at the end of this sentence and which are herein incorporated by reference. Kramer et al Invasion of reconstituted basement membrane matrix by metastatic tumor cells. Cancer Res. 46: 1989–1989,1986; and Albini et al A Rapid in vitro assay for quantitating the invasive potential of tumor cells. Cancer Res. 3239–3245, 198. Modifications were made to permit evaluation of pharmacologic effectors in this system and to increase screening throughput.

Polyvinylpyrrolidone-free polycarbonate filters (25×80 mm; 8 μm pore size (Nucleopore, Pleasantan, Calif.) were coated with 100 μg human fibronectin (Boehringer-Mannheim Corp., Indianapolis, Ind.) for 1 hour, permitted to air dry 5 to 10 minutes, and then coated overnight with Matrigel (500 μg/filter; Collaborative Research, Bedford, Mass.). Filters were then rehydrated with serum-free DMEM and assembled into 48-microwell chemotaxis chambers (Neuroprobe, Cabin Johbn, Md.). See Blood et al Identification of a tumor cell receptor for VGVAPG, an elastin-derived chemotactic peptide. J. Cell Biol. 107:1987–1994, 1988 which is herein incorporated by reference. Compounds tested were placed in upper wells of the chambers with HT1080 human fibrosarcoma cells (3.5×104 cells/well). For primary screens the final concentration of compounds was 45 μg/ml.

Chambers were incubated for 5 hours at 37° C. in a 5% $CO_2$ humidified atmosphere. After incubation chambers were disassembled and the filters were fixed and stained with Diff-Quik reagents (Baxter Scientific, McGaw Park, Ind.). Tumor cells that adhered to filters but failed to traverse the Matrigel barrier were wiped away with cotton swabs. The filter was then mounted between 2 glass slides and tumor cells that had invaded the Matrigel barrier in each microwell were quantitated as "% area covered by cells" with a Cue-2 Image Analysis System (Olympus Corp., Lake Success, N.Y.). When assayed under these conditions HT1080 cells (with or without Dimethylsulfoxide (DMSO) as a vehicle control) typically invade such that 34–40% surface is covered by cells and an invasion to this degree is defined as 100% invasion for the purposes of this test. Effects of compounds on the invasion are expressed as % inhibition based on the value obtained with vehicle control. Data obtained from this test are shown just below.

TABLE II

TUMOR CELL INVASION ASM

| COMPOUND NO. | Cell Invasion Assay % inhibition @ 45 μgmL$^{-1}$ |
|---|---|
| 1 | N.T. |
| 2 | 35% |
| 13 | 26% |
| 14 | N.T. |
| 3 | 48% |
| 4 | 86% |
| 6 | 66% |
| 5 | 46% |
| 7 | 0% |
| 8 | 46% |
| 9 | 52% |
| 10 | 72% |

TABLE II-continued

TUMOR CELL INVASION ASM

| COMPOUND NO. | Cell Invasion Assay % inhibition @ 45 μgmL$^{-1}$ |
|---|---|
| 15 | 30% |
| 16 | 46% |
| 17 | 53% |
| 18 | 18% |
| 19 | 100% |
| 11 | 42% |
| 12 | 20% |
| 23 | 57% |

N.T. means not tested.

The above data show that the compounds are useful as anti-metastatic agents and are therefore useful as anti-tumor agents.

The anti-psoriatic activity of the compounds of formula I of the invention may be demonstrated in the following experimental protocol.

Inhibition of Superoxide Generation in Human Neutrophils

One of the histological changes which occurs in psoriasis is infiltration of neutrophils into epidermis and dermis. Superoxide (SO) generation by neutrophils causes oxidative tissue damage during inflammatory processes. PKC plays an essential role in SO release in neutrophils. Formyl peptides (fMLP), important chemoattractants involved in cell recruitment to local inflammatory sites, promote the release of SO anion. The tumor promoting phorbol ester, phorbol-12 myristate-13-acetate (PMA), also induces SO release. Inhibitory activity on SO by the compounds of the invention, as can be seen from the data below, shows that they are useful as anti-inflammatory agents.

Neutrophils were prepared from human peripheral blood. SO release was induced by fMLP (100 nM) or PMA (100 nM) and measured as SO dismutase-inhibitable reduction of cytochrome c. Preincubation of the compound tested with $3-5 \times 10^6$ cells was for 15 minutes in the presence of cytochalasin B (5 MM) before addition of the stimulant, fMLP or PMA. 15 minutes after stimulation at 37° C., the reaction was stopped. The quantity of SO anion release was determined as the difference between the absorbance at 550 nm in the presence and absence of SO dismutase.

Antiinflammatory activity of the compounds of the invention was determined by use of the processes set forth in the following literature which is hereby incorporated by reference. Fischer et al Carcinogenesis 11:6, 9912–996(1990); and Gupta et al Soc. Inv. Dermotol 91:5, 486–491, 1988 and Nakadate et al J. Pharmacolo. 38 161–168,(1985); and Viaje et al Cancer Res. 37,1530–1536, 1977.

The results are given below.

TABLE III

NEUTROPHIL TEST

| COMPOUND NO. | IC$_{50}$ mM |
|---|---|
| 18 | >10 |
| 17 | >10 |
| 20 | >10 |
| 26 | 1.6 |
| 23 | 0.9 |

The above results show that compounds of the invention are useful as anti-inflammatory agents.

Mouse Skin Assay

Anti-inflammatory activity of the compounds of the invention were demonstrated in the mouse skin assay described just below.

Mice were treated first with compounds dissolved in acetone (25 µl), and then 30 seconds with TPA (12.5 µl). Blister formation was evaluated 18 hours after treatment. Each mouse was scored on a scale of 1–4 where 4 equals presence of a complete blister, 3 equals slight reduction in blister formation, 2 equals a 50% reduction in blister formation and 1 equals a complete absence of blisters. The data obtained from this test are shown in the table given just below. Based upon this visual evaluation, a compound was classified either as active or inactive.

TABLE IV

MOUSE SKIN ASSAY

| Compound | Mouse Skin |
|---|---|
| 26 | inactive |
| 23 | active |

These data show that the compounds of the invention are useful as antiinflammatory compounds. These data also show that the compounds of the invention are anti-psoriatic agents.

$^3$H Thymidine Uptake in Normal Human Keratinocytes (NHEK): Effects of Compounds of the Invention Biological activity of the compounds of the invention can be demonstrated by running the following test procedure. Second passage NHEK cells grown in MCDB 153 media with a 5% $CO_2$ air mixture at 37° can be used for experiments. Compounds of the invention can be prepared as 5 mM stock solutions in DMSO. Cells should be grown to 60–80% confluency in 6 well trays. Compounds can be added to give a concentration of $5\times10^{-6}$ molar and cultures can be simultaneously pulsed with 1 microCurie/mL $^3$H thymidine for 20 hours. Cells can be harvested and tritium can be counted using a liquid scintillation counter; results can be the average of 8 wells per compound. In the control, when no compound is employed, there should be 0% inhibition of thymidine uptake. By following the just above described test procedure, it can be demonstrated that the compounds of the invention are anti-psoriatic agents.

The compounds of this invention can be administered in any number of conventional dosage forms, e.g., topical, oral, parenteral, rectal, transdermal, and the like. Oral or rectal dosage forms include capsules, tablets, pills, powders, cachets, and suppositories. Liquid oral dosage forms include solutions and suspensions. Parenteral preparations include sterile solutions and suspensions. Topical dosage forms can be creams, ointments, lotions, transdermal devices (e.g., of the conventional patch or matrix type) and the like.

The formulations and pharmaceutical compositions contemplated by the above dosage forms can be prepared with conventional pharmaceutically acceptable excipients and additives, using conventional techniques. Such pharmaceutically acceptable excipients and additives are intended to include carriers, binders, flavorings, buffers, thickeners, coloring agents, stabilizing agents, emulsifying agents, dispersing agents, suspending agents, perfumes, preservatives lubricants, etc.

Suitable pharmaceutical acceptable solid carriers are magnesium carbonate, magnesium stearate, talc, sugar, lactose, pectin, dextrin, starch, gelatin, tragacanth, methylcellulose, sodium carboxymethylcellulose, low melting waxes, cocoa butter and the like. Capsules can be made wherein the active compound is inserted into the capsules along with a pharmaceutically acceptable carrier. The active compounds of this invention can be mixed with pharmaceutically acceptable excipients or be used in finely divided powder form without excipients for inclusion into the capsules. Similarly, cachets are included.

Liquid form preparations include solutions, suspensions and emulsions such as water or water-propylene glycol solutions for parenteral injection. Liquid preparations can also be formulated in solution in polyethylene glycol and/or propylene glycol, which may contain water. Aqueous solutions suitable for oral use can be prepared by adding the active component in water and adding suitable colorants, flavors, stabilizing, sweetening, solubilizing and thickening agents as desired. Aqueous suspensions suitable for oral use can be made by dispersing the active component in finely divided form in water with viscous material, i.e., pharmaceutically acceptable natural or synthetic gums, resins, methylcellulose, sodium carboxymethylcellulose and other well-known suspending agents.

Formulations for topical application may include the above liquid forms, as well as creams, aerosols, sprays, dusts, powders, lotions and ointments which are prepared by combining an active ingredient according to this invention with conventional pharmaceutical acceptable diluents and carriers commonly used in topical, dry, liquid, cream and aerosol formulations. Ointment and creams may, for example, be formulated with an aqueous or oily base with the addition of suitable thickening and/or gelling agents. Such bases may, thus, for example, include water and/or an oil such as liquid paraffin or a vegetable oil such as peanut oil or castor oil. Thickening agents which may be used according to the nature of the base include soft paraffin, aluminum stearate, cetostearyl alcohol, propylene glycol, polyethylene glycols, woolfat, hydrogenated lanolin, beeswax, etc.

Lotions may be formulations with an aqueous or oil base and will, in general, also include one or more of pharmaceutically acceptable stabilizing agents, emulsifying agents, dispersing agents, suspending agents, thickening agents, coloring agents, perfumes and the like.

Powders may be formed with the aid of any suitable pharmaceutically acceptable powder base, e.g., talc, lactose, starch, etc. Drops may be formulated with an aqueous base or nonaqueous base also comprising one or more pharmaceutically acceptable dispersing agents, suspending agents, solubilizing agents, etc.

The topical pharmaceutical compositions may also include one or more preservatives or bacteriostatic agents, e.g., methyl hydroxybenzoate, propyl hydroxybenzoate, chlorocresol, benzalkonium chlorides, etc.

The topical pharmaceutical compositions may also contain an active compound of this invention in combination with other active ingredients such as antimicrobial agents, particularly antibiotics, anesthetics, analgesics and antipruritic agents.

Also included are solid form preparations which are intended to be converted, shortly before use, to liquid form preparations for either oral or parenteral administration. Such liquid forms include solutions, suspensions and emulsions. These particular solid form preparations are most conveniently provided in unit dose form and as such are used to provide a single liquid dosage unit. Alternatively, sufficient solid may be provided so that after conversion to liquid form, multiple individual liquid doses may be obtained by measuring predetermined volumes of the liquid form preparation as with a syringe, teaspoon or other volumetric container. When multiple liquid doses are so prepared, it is preferred to maintain the unused portion of said liquid doses under conditions which retard possible decomposition. The solid form preparations intended to be converted to liquid form may contain, in addition to the active material, pharmaceutically acceptable flavorants, colorants, stabilizers, buffers, artificial and natural sweeteners, dispersants, thickeners, solubilizing agents and the like. The solvent utilized for preparing the liquid form preparation may be water, isotonic water, ethanol, glycerine, propylene glycol and the like as well as mixtures thereof. Naturally, the solvent utilized will be chosen with regard to the mute of administration, for example, liquid preparations containing large amounts of ethanol are not suitable for parenteral use.

The compounds of this invention may also be deliverable transdermally for systemic distribution. The transdermal compositions can take the form of creams, lotions and/or emulsions and can be included in a transdermal patch of the matrix or reservoir type as are conventional in the art for this purpose.

A composition of the invention comprises a therapeutically effective amount of a compound of the invention in combination with a pharmaceutically acceptable carrier material.

The compounds of this invention may be administered by any conventional mode of administration by employing a therapeutically effective amount of a compound of this invention for such mode. The dosages may be varied depending upon the requirements of the patient in the judgment of the attending clinician, the severity of the condition being treated and the particular compound being employed. Determination of the proper dosage for a particular situation is within the skill of the art. Treatment can be initiated with smaller dosages which are less than the optimum dose of the compound. Thereafter, the dosage should be increased by small increments until the optimum effect under the circumstances is reached. For convenience, the total daily dosage may be divided and administered in portions during the day if desired.

An oral dosage range for the compounds of the invention is from about 0.1 mg/kg to about 100 mg/kg. A parenteral dosage range for the compounds of the invention is from about 0.1 mg/kg to about 30 mg/kg.

EXAMPLES

Example 1

14,15-Dicyano-6H,8H-diindolo[1,2,3-ef:3',2',1'-jk]-3,1,5-benzotriazepine

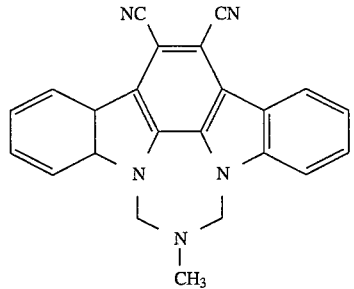

In a 25 mL round bottomed flask, were placed 6.0 mL of glacial acetic acid and 0.20 g of 37 wt. % solution of formaldehyde in water. The solution was cooled to 10° C. and 0.12 mL of a 40 wt % solution of methyl amine in water was added via syringe. The mixture was stirred for 15 minutes and 0.40 g of 11,12-dicyano indolocarbazole was added all at once. After heating the resulting mixture at 65° C. for 2 hours, 6.0 mL of ice water was added and the tan precipitate was collected by suction filtration and washed with 2×5.0 mL of water. After drying under vacuum (1.0 mm Hg) for 24 hours, 0.38 g of the title compound was collected.

Example 2

10,11-Dihydro-3-imino-10-methyl-1H,9H-diindolo [1,2,3,-ef:3',2',1'-jk]pyrrolo-[3,4-h][1,3,5] benzotriazepin-1(2H)-one

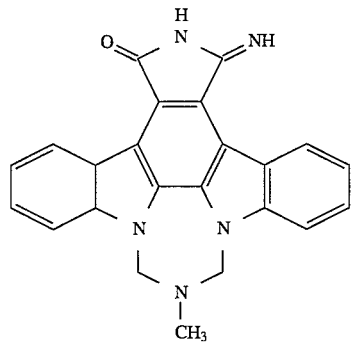

In a 25 mL round bottomed flask, equipped with a reflux condenser, were placed 0.38 g of the compound of Example 1, 10 mL of dimethyl sulfoxide and 0.8 mL of a 50 wt. % solution of KOH in water. The solution was heated at 100° C. for 50 minutes, cooled to room temperature and diluted with 20 mL of water. The precipitate was collected by suction filtration and washed with 5.0 mL of water to give 0.30 g of the title compound.

decomp. p.: 271°–273° C.; ms(El): 379.1,336.1(100% peak)

Example 3

10,11-Dihydro-10-methyl-1H,9H-diindolo[1,2,3-ef:3',2',1'-jk]pyrrolo[3,4-h][1,3,5]benzotriazepin-1,3-(2H)-dione

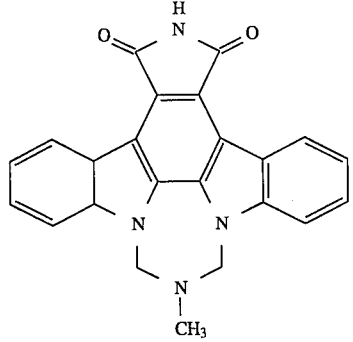

In a 25 mL round bottomed flask, were placed 0.30 g of the compound of Example 2, 5.0 mL of dimethyl sulfoxide and 0.25 mL of water. Five drops of trifluoroacetic acid were added and the solution was stirred for 1 hour. Addition of 15 mL of water generated a precipitate that was collected by suction filtration. The precipitate was dried under vacuum (1.0 mm Hg) to give 0.23 g of the title compound.

decomp. p.: 328°–330° C.; ms(FAB): 380(54%), 337(39%)

Example 4

7-Benzyloxy-14,15-dibromo-6H,8H-diindolo[1,2,3-ef:3',2',1'-jk]-3,1,5-benzotriazepine

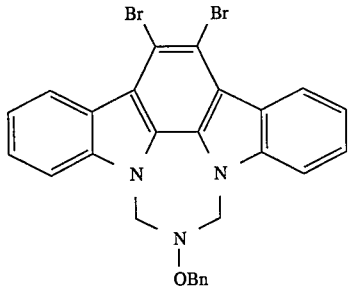

In a 50 mL round bottomed flask, were placed 10.0 mL of glacial acetic acid and 0.77 g of 37 wt. % formaldehyde in water. A solution of O-benzylhydroxylamine was formed (by adding 1.91 mL of a 2M aqueous NaOH solution to a suspension of 760 mg of O-benzylhydroxylamine hydrochloride in 2 mL of water) and added to the cooled solution. After stirring for 15 minutes at 10° C., 1.97 g of 11,12-dibromoindolocarbazole was added all at once, followed by 10 mL of glacial acetic acid and the mixture was stirred at room temperature for 12 hours. The precipitate was collected by suction filtration, washed with 2×10 mL water, air dried for 4 hours and purified by flash chromatography on silica gel (2:1 hexane:dichloromethane). After evaporation of the solvent, 1.66 g of the title compound was collected.

Example 5

7-Benzyl-14,15-dibromo-6H,8H-diindolo[1,2,3-ef:3',2',1'-jk]-3,1,5-benzotriazepine

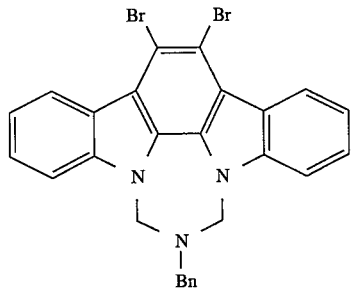

In a 25 mL round bottomed flask, were placed 79 mg of a 37 wt. % solution of formaldehyde in water and 2.0 mL of glacial acetic acid. The solution was cooled to 10° C., 0.052 mL of benzyl amine was added and the resulting solution was stirred 15 minutes at 10° C. 11,12-Dibromoindolocarbazole (0.20 g) was added all at once and the mixture was stirred at room temperature for 2 hours, diluted with ice water and the tan precipitate was collected by suction filtration. After drying under vacuum (1.0 mm Hg) for 16 hours, 0.21 g of the title compound was collected.

Example 6

7-Benzyl-14,15-dicyano-6H,8H-diindolo[1,2,3-ef:3',2',1'-jk]-3,1,5-benzotriazepine

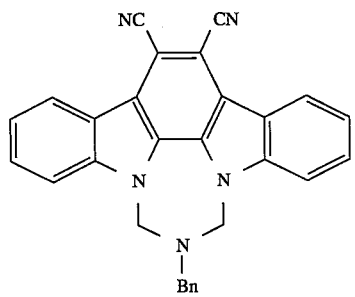

In a 25 mL round bottomed flask, equipped with a reflux condenser, was placed 0.21 g of the compound of Example 5, 105 mg of sodium iodide, 349 mg of CuCN and 10 mL of N,N-dimethyl acetamide. The mixture was heated at 190° C. for 4 hours, cooled to room temperature and diluted with 100 mL dichloromethane, 100 mL water and 12 mL concentrated NH4OH. After stirring rapidly for 15 minutes, the mixture was filtered and the liquid portion was transferred to a separatory funnel. The dichloromethane layer was removed, washed with brine and added over $K_2CO_3$. After filtration and evaporation of volatile solvents, the remaining liquid portion was treated with 8 mL of hexane and the resulting precipitate was collected by suction filtration to give 0.11 g of the title compound.

Example 7

10-[2-Amino(2-methyl-2-propoxy)carbonyl]ethyl-10,11-dihydro-2-[tri(1-methylethyl)silyl]-1H,9H-diindolo[1,2,3-ef:3',2',1'-jk]pyrrolo[3,4-h][1,3,5]benzotriazepin-1,3-(2H)-dione

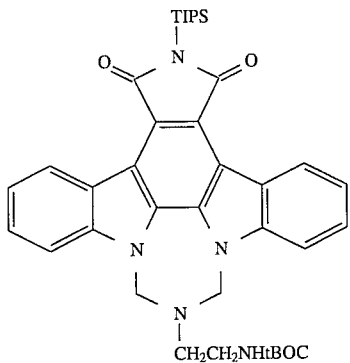

In a 25 mL round bottomed flask, were placed 2.0 mL of glacial acetic acid and 60 mg of 37 wt. % solution of formaldehyde in water. The solution was cooled to 10° C. and 60 mg of N-(2-methyl-2-propoxy)carbonyl ethylene diamine in 1.0 mL of glacial acetic acid was added via syringe. The mixture was stirred for 10 minutes and 177 mg of 2-[tri(1-methylethyl)silyl] Arcyriaflavin A was added all at once. After heating the resulting solution at 65° C. for 2 hours, 6.0 mL of ice water was added and the yellow precipitate was collected by suction filtration and washed with 2×5.0 mL of water. After drying under vacuum (1.0 mm Hg) for 24 hours, 0.13 g of the title compound was collected.

Example 8

10-[2-Amino(2-methyl-2-propoxy)carbonyl]ethyl-10,11-dihydro-1H,9H-diindolo[1,2,3-ef:3',2',1'-jk]pyrrolo[3,4-h][1,3,5]benzotriazepin-1,3-(2H)-dione

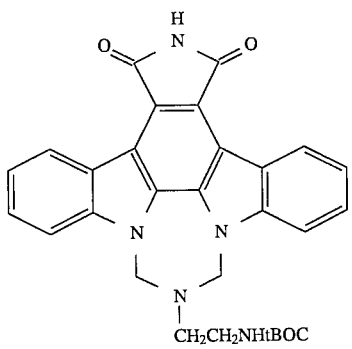

In a 5 mL round bottomed flask were placed 0.07 g of the compound from Example 7, 1.0 mL of THF and 0.15 mL of a 1.0M solution of tetra-n-butyl ammonium fluoride in THF. After stirring for 7 minutes at room temperature, the reaction solution was diluted with 5.0 mL of water, extracted with dichloromethane, washed with water and brine and added over $MgSO_4$. After filtration and evaporation of the solvent, 0.04 g of the title compound was collected as a yellow solid. decomp. pt.: slow decomp.>250° C.; HRMS: calc'd: 509.2063; measured: 509.2073

Example 9

2,3,10,11-tetrahydro-10-H-1H,9H-diindolo[1,2,3-ef:3',2',1'-jk]pyrrolo[3,4-h][1,3,5]benzotriazepin-1,3-(2H)-dione

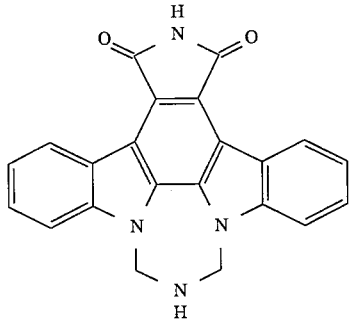

In a 25 mL round bottom were placed 8 mL of THF, 12 mL of EtOH and 0.03 g of the compound from Example 32. The resulting solution was added to 0.21 g of Raney nickel and the mixture was heated at 65° C. for 16 hours. After cooling to room temperature, the catalyst was removed by filtration through Celite and the solvents evaporated to give 0.15 g of the title compound. decomp. pt.: 325°–327° C.; ms(El): 366(41%),337(100%); HRMS: calc'd: 366.1117; measured: 366.1134

Example 10

1H,9H,11H-2,3-Dihydro-10-methyl-diindolo[1,2,3-ef:3',2',1'-jk]pyrrolo[3,4-h][3,1,5]benzotriazepin-3-one

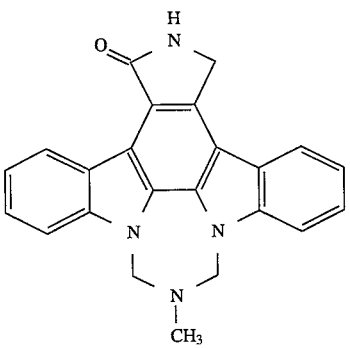

In a 25 mL round bottom, are placed 0.2 g of 10,11-dihydro-3-imino-10-methyl-1H,9H-diindolo[1,2,3-ef:3',2',1'-jk]pyrrolo[3,4-h][1,3,5]benzotriazepin-1(2H)-one, 15 mL of glacial acetic acid and 0.16 g of sodium cyanoborohydride. The mixture is heated at 60° C. for 1 hour, then cooled to room temperature. Ice water is slowly added and the resulting precipitate is collected by suction filtration, washed with water and dried under vacuum (1.0 mm Hg) to give 0.16 g of the title compound. Decomposition point: 2300°–232° C. compound goes from tan to black; HRMS: calcd 366.1481; found 366.1483.

Example 11

10,11-Dihydro-10-[2-amino]ethyl-1H,9H-diindolo[1,2,3-ef:3',2',1'-jk]pyrrolo[3,4-h][1,3,5]benzotriazepin-1,3-(2H)-dione

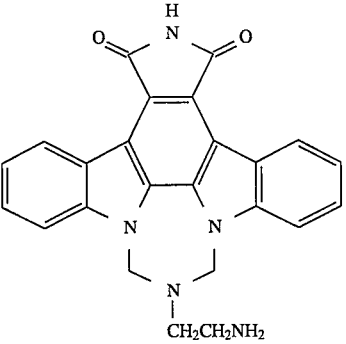

In a 5 mL round bottomed flask were placed 0.05 g of the compound from Example 8, 2.0 mL of dichloromethane and 0.20 mL of trifluoroacetic acid. After stirring at room temperature for 5 minutes, the reaction solution was poured into 0.5 g of solid $NaHCO_3$ and 4 g of ice was added. The resulting mixture was partitioned between water and dichloromethane, the dichloromethane extracts were dried over $K_2CO_3$, filtered and evaporated to give 0.04 g of the title compound.

Example 12

6H,8H-Diindolo[1,2,3-ef:3',2',1'-jk]-3,1,5-benzoxazine

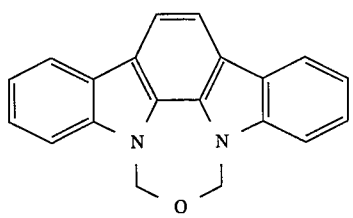

In a 50 mL round bottomed flask were placed 0.26 g of indolocarbazole, 50 mL of THF, 0.5 mL of Aliquat® 336 (as a 20 wt % solution acetonitrile) and 0.15 mL of bis(chloromethyl) ether. This solution was stirred rapidly and 10 mL of a 50 wt % solution of NaOH in water was added, all at once. After stirring for 20 minutes, 0.15 mL of bis(chloromethyl) ether was added and the resulting mixture was stirred rapidly for 1 hour. Water (10mL) was added and the $CH_2Cl_2$ layer was collected and added over $MgSO_4$. After suction filtration, the solvent was removed in vacuo and the resulting solid was purified by column chromatography (silica gel; 2:1 hexane:ethyl acetate) to give 0.10 g of the title compound.

Example 13

14,15-Dibromo-6H,8H-diindolo[1,2,3-ef:3',2',1'-jk]-3,1,5-benzoxazine

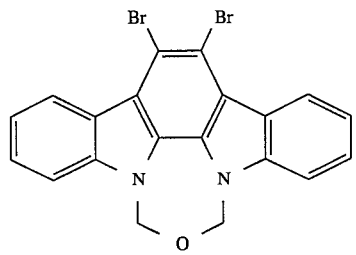

In a 250 mL round bottomed flask were placed 0.74 g of the title compound of Example 12 and 20 mL of dimethyl formamide and the solution was cooled to 0° C. N-Bromosuccinimide (0.88 g) was added in four portions over a 10 minute period, the cooling bath was removed and stirring was continued for 40 minutes. The reaction solution was poured into 60 mL of an ice cold aqueous solution of $Na_2SO_3$ and the resulting precipitate was collected and washed with water (2×25 mL). After drying in a vacuum oven at room temperature for 24 hours, 1.00 g of the title compound was collected.

Example 14

2,3-Dihydro-3-imino-1H,9H,11H-diindolo[1,2,3-ef:3',2',1'-jk}pyrrolo[3,4-h][3,1,5]-benzoxadiazepin-1-one

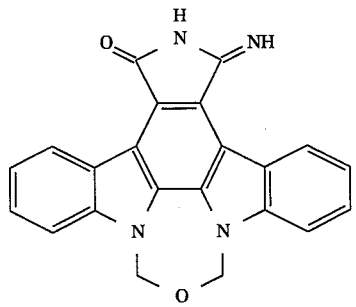

The compound of Example 13 (0.50 g) was subjected to the reaction conditions outlined in Example 6 and then Example 2 to give 0.28 g of the title compound. decomp, pt.: 227°–233° C.; MS(FAB): 367 (70%), 368(24%)

Example 15

1H,9H,11H-Diindolo[1,2,3-ef:3',2',1'-jk]pyrrolo[3,4-h][3,1,5]-benzoxadiazepin, 1,3(2H)-dione

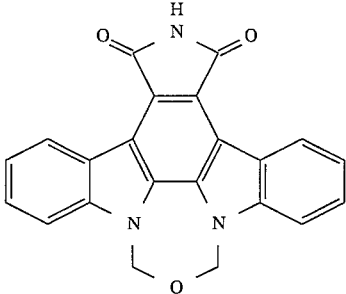

The compound of Example 14 (0.28 g) was subjected to the reaction conditions outlined in Example 3 to give 0.13 g of the title compound. decomp. pt.: slow decomp. above 327° C.; MS(El): 367(56%), 368(13%)

Example 16

2-Triisopropyl silyl Arcyriaflavin A

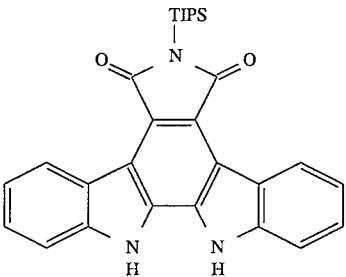

In a 2 L round bottomed flask were placed 5.0 g of Arcyriaflavin A, 1.5 L of dichloromethane and 3.0 mL of N,N-diisopropyl ethylamine. After stirring at room temperature for 30 minutes, 4.54 mL of triisopropyl silyl triflate was added and stirring was continued for 5 days. The reaction mixture was filtered and to the filtrate was added 5.0 g of Celite. The solvents were removed in vacuo and the resulting mixture was purified by column chromatography, eluting with 1:1 dichloromethane: hexanes. After solvent evaporation, there remained 3.23 g of the title compound.

Example 16a

2-Triisopropyl silyl Arcyriaflavin A

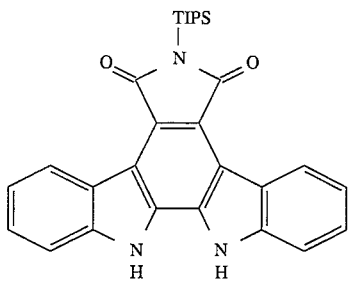

In a 500 ml round bottom flask were placed 5.04 g of Arcyriaflavin A, 100 mL of THF 3.24 mL of N,N-diisopropylethylamine and 1.97 g of N,N-dimethyl-trifluoroacteamide. The resulting solution was stirred at room temperature and 4.17 ML of triisopropyl silyl triflate was added dropwise. After stirring for 4 hours, the reaction was diluted with EtOAc, washed with water, brine and dried over MgSO$_4$. After filtration and evaporation of solvents, the solid crude was adsorbed onto 5.0 Celite and chromatographed on silica eluting with 4:2:1 CH$_2$Cl$_2$:hexane: EtOAc. After evaporation, 4.86 g of the title compound were collected as a yellow solid.

Example 17

14,15-Dicyano-6H,8H-diindolo[1,2,3-ef:3',2',1'-jk]3,1,5-benzothiazine

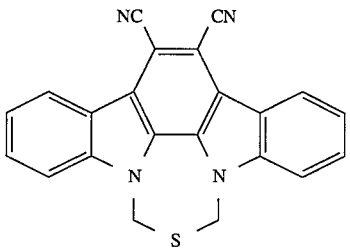

In a 250 mL round bottomed flask were placed 1.20 g of 11,12-dicyano indolocarbazole, and 200 mL of dimethyl formamide. Sodium hydride (0.47 g) was added and the mixture was stirred for 15 minutes at which time 0.47 mL of bischloromethyl sulfide was added dropwise. The mixture was stirred for 20 hours, 1.0 g of ice was slowly added and when gas evolution ceased, 600 mL of ice water was added. The resulting precipitate was collected, washed with water and dried in vacuo to give 0.29 g of the title compound.

Example 18

1H,9H,11H-1-Imino-2,3-dihydro-diindolo
[1,2,3-ef:3',2',1'-jk]pyrrolo-[3,4-h][3,1,5]-
benzothiadiazepine-3-one

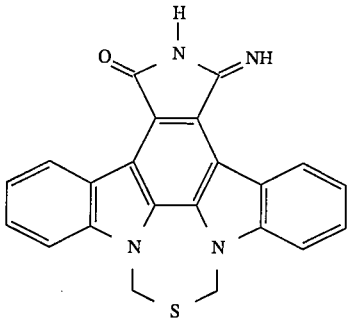

The compound from Example 17 (0.13 g) was subjected to the reaction conditions of Example 2 to give 0.12 g of the title compound. decomp.pt.: 272°–274° C. (yellow to black); MS(El): 382(84%),383(23%)

Example 19

1H,9H,11H-Diindolo[1,2,3-ef:3',2',1'-jk]pyrrolo-
[3,4-h][3,1,5]- benzothiadiazepine-1,3-(2H)-dione

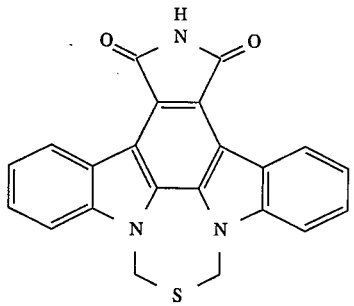

The compound from Example 18 (0.11 g) was subjected to the reaction conditions of Example 3 to give 0.06 g of the title compound. decomp. pt.: 339°–341° C. (yellow to brown); HRMS: Calc'd: 383.0728; Measured: 383.0739

Example 20

1H,9H,11H-2,3-Dihydro-diindolo[1,2,3-ef:3',2',1'-jk]
pyrrolo-[3,4-h][3,1,5]-benzothiadiazepine-3-one

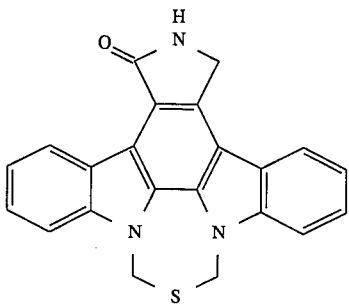

In a 250 mL round bottomed flask were placed 0.07 g of the compound of Example 18, 15 mL of glacial acetic acid and 0.06 g of sodium cyanoborohydride was added. The reaction mixture was heated at 60° C. for 1 hour, ice water was slowly added and the resulting precipitate was collected by suction filtration and washed with water. The solid was further purified by column chromatography on silica gel with a 20:1 dichloromethane:ethyl acetate eluant. After evaporation of the solvent, 0.05 g of the title compound was collected. decomp. pt.: 275°–277° C. (yellow to black); HRMS: calc'd: 369.0936; measured: 369.0924

Example 21

1H,9H,11H-10-Oxo-diindolo[1,2,3-ef:3',2',1'-jk]
pyrrolo-[3,4-h][3,1,5]-benzothiadiazepine-
1,3-(2H)-dione

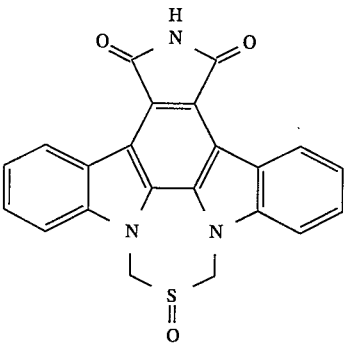

In a 50 mL round bottomed flask were placed 0.15 g of the compound from Example 19 and 15 mL of DMF and the solution was cooled to 0° C. Meta-chloroperoxybenzoic acid (0.04 g) was added and the solution was stirred for 2 hour at 0° C. and then at room temperature for 1 hour. A solution of 70 mL of water, 0.10 g of sodium bicarbonate and 0.14 g of sodium sulfite was added and the mixture was extracted with dichloromethane. After drying over $MgSO_4$ and removal of solvent in vacuo, the resulting solid was chromatographed on silica gel eluting with 50:1 dichloromethane:methanol to give 0.03 g of the title compound. decomp. pt.: 250°–252° C.(tan to black); HRMS: calc'd: 399.0678; measured: 399.0673

Example 22

1H,9H,11H-Diindolo[1,2,3-ef:3',2',1']pyrrolo-
[3,4-h][3,1,5]-benzothiadiazepine-1,3(2H)-dione
10,10-dioxide

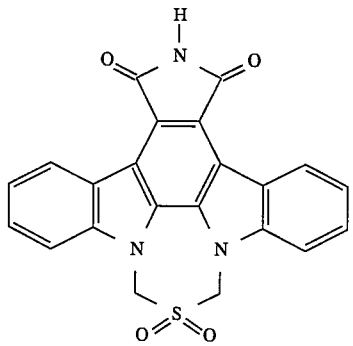

In a 50 mL round bottomed flask were placed 0.04 g of the compound from Example 19, 20 mL of DMF and 0.05 g m-chloroperoxybenzoic acid. After 2 hour, 0.05 g of m-chloroperoxybenzoic acid was added and the resulting solution was stirred overnight. A solution containing 50 mL of water, 0.03 g of sodium bicarbonate and 0.04 g of sodium sulfite was added and the mixture was extracted with dichloromethane. The crude product precipitated from solution and was collected by suction filtration and chromatographed on silica gel, eluting with 50:1 dichloromethane:ethyl acetate to give 0.03 g of the title compound. decomp. pt.: 307°–309° C. (tan to black); HRMS: calc'd: 416.0705; measured: 416.0708

Example 23

1H,9H,11H-1-Hydroxy-2,3-dihydro-diindolo[1,2,3-ef:3',2',1'-jk]pyrrolo-[3,4-h][3,1,5]-benzothiadiazepine-3-one

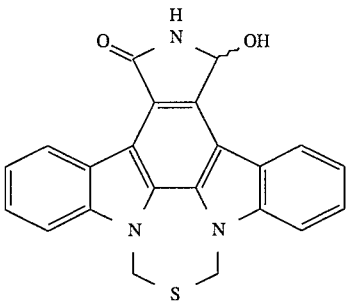

In a 25 mL round bottomed flask were placed 0.27 g of the compound from Example 19 and 5 mL of THF and 0.05 g of lithium aluminum hydride was added in one portion. After stirring at room temperature for 17 hour, 5.0 mL of 1.0M NaOH was added and the resulting mixture was extracted with dichloromethane. The organic extracts were washed with water and brine and dried over $Na_2SO_4$. After evaporation of the solvent, the crude product was chromatographed on silica gel, eluting with 30:1 dichloromethane:methanol to give 0.21 g of the title compound MS[FAB] 386(65%)385(75%)368(100%).

Example 24

1H,9H,11H-2,3-Dihydro-diindolo[1,2,3-ef:3',2',1'-jk]pyrrolo-[3,4-h][3,1,5]-benzothiadiazepine-3-one

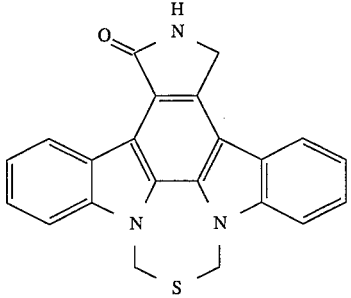

In a 25 mL round bottomed flask were placed 0.17 g of the compound from Example 23, 5.0 mL of THF and 0.25 mL of a 1.0M solution of $BH_3$ in THF. After stirring for 18 hours at room temperature, 1.0 mL of a 10% aqueous solution of acetic acid was slowly added and the solution was stirred for 20 minutes. Water (10 mL) and 20 mL of ethyl acetate were added, the organic extracts were combined and washed with water, brine and dried over MgSO4. Evaporation of the solvent gave 0.13 g of the title compound. (Characterization data as for Example 20)

Example 25

2-Triisopropyl silyl-1H,9H,11H-diindolo[1,2,3-ef:3',2',1'-jk]pyrrolo-[3,4-h][3,1,5]-benzothiadiazepine-1,3,-(2H)-dione

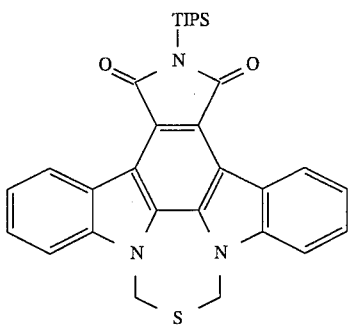

In a 500 mL round bottomed flask were placed 1.2 g of the compound from Example 16 and 125 mL of THF and to this solution was added 0.5 g of NaH. The mixture was stirred for 15 minutes and 0.30 mL of bischloromethyl sulfide was added dropwise. After stirring for 20 hours, 1.0 g of ice was added cautiously and then 500 mL of ice water. After 30 minutes, the precipitate was collected by suction filtration and chromatographed on silica gel, eluting with 2:1 hexanes:dichloromethane to give, after evaporation of the solvents, 0.77 g of the title compound.

Example 26

2-Triisopropyl silyl-1H,9H,11H-diindolo[1,2,3-ef:3',2',1'-jk]pyrrolo-[3,4-h][3,1,5]-benzothiadiazepine-1,3(2H)-dione 10,10-dioxide

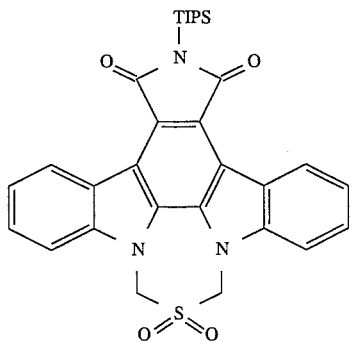

In a 50 mL round bottomed flask were placed 0.40 g of the compound from Example 25, 8 mL of dichloromethane and 0.25 g m-chloroperoxybenzoic acid. After 2 hours, 0.08 g of m-chloroperoxybenzoic acid was added and the resulting solution was stirred overnight. A solution containing 50 mL of water, 0.03 g of sodium bicarbonate and 0.04 g of sodium sulfite was added and the mixture was extracted with dichloromethane. The crude product precipitated from solution and was collected by suction filtration to give 0.39 g of the title compound.

Example 27

9-Methyl-2-triisopropyl silyl-1H,9H,11H-diindolo[1,2,3-ef:3',2',1'-jk] pyrrolo-[3,4-h][3,1,5]-benzothiadiazepine-1,3(2H)-dione 10,10-dioxide

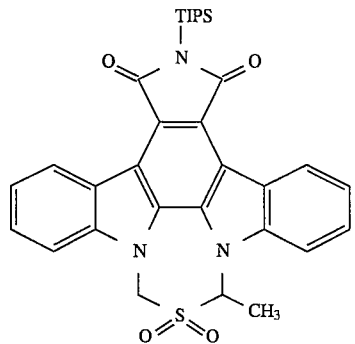

In a 25 mL round bottomed flask were placed 0.05 g of the compound from Example 26 and 5.0 mL of THF and the solution was cooled to −78° C. (bath temperature). A 1.0M solution of Na(NSi(CH$_3$)$_3$)$_2$ in THF was added dropwise (0.086 mL). After stirring for 20 minutes at low temperature, methyl iodide was added and the solution was stirred for 1 hour more. Solid NH$_4$Cl was added and the reaction allowed to warm to room temperature. The resulting mixture was partitioned between EtOAc and water and the organic extracts were combined, washed with brine, dried over MgSO$_4$, filtered, evaporated and chromatographed on silica gel, eluting with 2:1 hexanes:dichloromethane to give 0.03 g of the title compound.

Example 28

9,11-Dimethyl-2-triisopropyl silyl-1H,9H,11H-diindolo[1,2,3-ef:3',2',1'-jk] pyrrolo-[3,4-h][3,1,5]-benzothiadiazepine-1,3(2H)-dione 10,10-dioxide

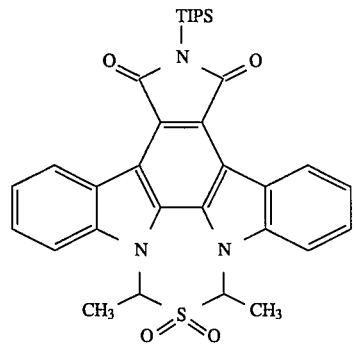

A 25 mL flask was charged with 0.7 mL of a 1.0M solution of NaN (Si(CH$_3$))$_2$ in THF and cooled to −78° C. A solution of 0.20 g of the compound from Example 26 and 5.0 mL of THF was added dropwise and the resulting mixture was stirred for 1.0 hour when 0.10 mL of MeI was added. The resulting mixture was stirred for 1.0 hour then warmed to room temperature and stirred for 4 hours. A saturated solution of NH$_4$Cl was added and the mixture was extracted with dichloromethane. The organic extracts were washed with water, brine, dried over MgSO$_4$, filtered and evaporated to give a crude oil which was purified by column chromatography (silica gel/eluant: hexane:dichloromethane:ethyl acetate, 100:10:1) to give 0.07 g of the title compound.

Example 29

9-Methyl-1H,9H,11H-diindolo[1,2,3-ef:3',2',1'-jk] pyrrolo-[3,4-h][3,1,5]-benzothiadiazepine-1,3(2H)-dione 10,10-dioxide

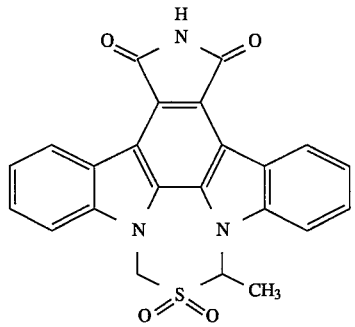

In a 10 mL flask was placed 0.17 g of the compound from Example 27, 8.0 mL of acetic acid, 2.0 mL of water and 0.10 g of sodium acetate. The resulting mixture was heated at 65° C. for 16 hours, cooled and poured into ice and water. The resulting yellow precipitate was collected, washed with water and dried in vacuo (2.0 mm Hg) for 2 days to give 0.08 g of the title compound.

Example 30

9,11-Dimethyl-1H,9H,11H-diindolo [1,2,3-ef:3',2',1'-jk]pyrrolo-[3,4-h][3,1,5]-benzothiadiazepine-1,3(2H)-dione 10,10-dioxide

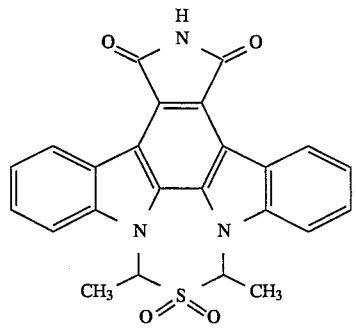

The compound from Example 28 (0.30 g) was subjected to the reaction conditions of Example 29, except the mixture was heated at 100° C. 0.17 g of the title compound was collected. HRMS calculated for C$_{24}$H$_{17}$N$_3$O$_4$S 443.0940 measured 443.0947.

Example 31

10-Hydroxy-10,11-dihydro-2-[tri(1-methylethyl)silyl]-1H,9H-diindolo[1,2,3-ef:3',2',1'-jk]pyrrolo[3,4-h][1,3,5]benzotriazepin-1,3-(2H)-dione

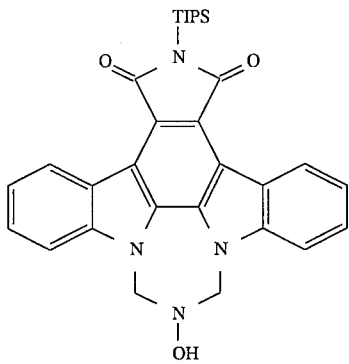

In a 25 mL round bottomed flask, were placed 2.0 mL of glacial acetic acid and 102 mg of 37 wt. % solution of formaldehyde in water. The solution was cooled to 10° C. and a mixture of 44 mg of hydroxylamine hydrochloride and 0.63 mL of a 1.0M aqueous solution of NaOH was added all at once. The mixture was stirred for 10 minutes and 205 mg of 2-[tri(1-methylethyl)silyl]Arcyriaflavin A was added all at once. After heating the resulting solution at 65° C. for 2 hours, 6.0 mL of ice water was added and the yellow precipitate was collected by suction filtration and washed with 2×5.0 mL of water. After drying under vacuum (1.0 mm Hg) for 24 hours, 0.20 g of the title compound was collected.

Example 32

10-Hydroxy-10,11-dihydro-1H,9H-diindolo[1,2,3-ef:3',2',1'-jk]pyrrolo[3,4-h][1,3,5]benzotriazepin-1,3-(2H)-dione

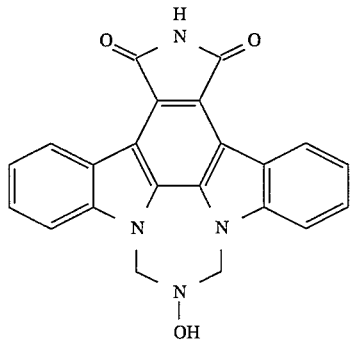

The title compound from Example 31 (0.20 g) was subjected to the reaction conditions outlined in Example 8 to give 0.18 g of the title compound. decomp. pt.: 280°–282° C. (yellow to brown); HRMS: calc'd for $C_{22}H_{14}N_4O_3$: 382.1066; observed: 382.1060.

Example 33

11,12-Dibromo indolocarbazole

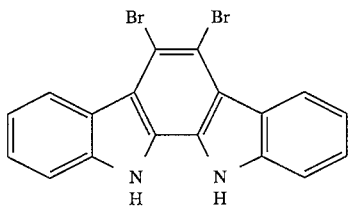

In a 500 mL flask were placed 120 mL of DMF and 5.00 g of indolocarbazole. The resulting solution was cooled to 0° C. in an ice bath and a solution of 13.10 g $Ph(Me)_3NBr.Br_2$ and 20 mL of DMF was added dropwise over a 15 minute period. The solution was poured into 300 mL of a 5% aqueous solution of $Na_2SO_3$ and the resulting tan precipitate was collected, washed with water and added in a vacuum oven (1.0 mm Hg) at room temperature for 4 days to give 7.00 g of the title compound.

Example 34

11,12-Dicyano indolocarbazole

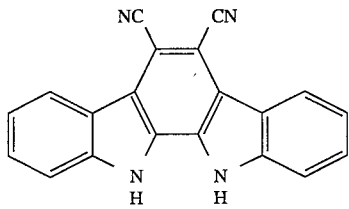

The compound from Example 33 (6.54 g) was subjected to the reaction conditions of Example 6 to give 3.26 g of the title compound.

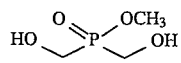

Example 35

Methyl bis(hydroxymethyl)phosphinate

In a 2.0 L flask were placed 155 mL of methanol, 570 mL of toluene and 7.70 g of bis(hydroxy methyl) phosphinic acid, which is a known compound. To the resulting solution was added trimethylsilyl diazomethane as a 2.0M solution in hexane at such a rate that the internal temperature was kept at or below 30° C. After approximately 100 mL had been added, the solution turned yellow and was stirred for 30 minutes. Acetic acid was added until the solution turned clear and the solvents were removed in vacuo to give 8.40 g of the title compound as a clear oil. MS(FAB): 140(11%), 141(100%)

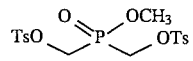

Example 36

Methyl bis(p-toluenesulfonyl methyl)phosphinate

The compound of Example 35 (0.62 g) was dissolved in 7.0 mL of pyridine and cooled in an ice-salt bath. P-Toluenesulfonyl chloride (1.71 g) was added all at once and the resulting solution was stirred at or below 14° C. for 6 hours. The pyridine was removed in vacuo and the resulting syrup was partitioned between ethyl acetate and cold water. The ethyl acetate extracts were washed with brine, dried over $Na_2SO_4$, filtered and evaporated to give a crude solid which was further purified by column chromatography (silica gel/ ethyl acetate:dichloromethane 1:20). The title compound was collected as a clear oil, 0.32 g. MS(FAB): 449(100%), 448(7%), 277(24%)

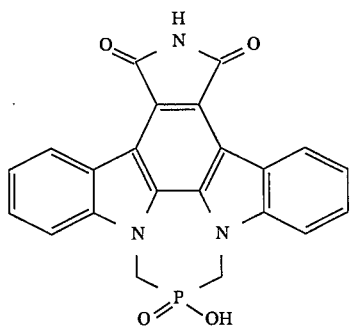

Example 37

1H,9H,11H-Diindolo[1,2-e:2,1-k]-pyrrolo[3,4-h][1,5,3] benzdiazaphosphepine-1,3(2H)-dione 10-oxide A solution of 1.01 g of the compound from Example 16 and 3.0 mL of THF were added dropwise to a cooled (0° C.) mixture of 0.21 g of NaH in 1.0 mL of THF. The resulting blood red suspension was stirred at room temperature for 45 minutes and cooled to 0° C. A solution of 0.94 g of the compound from Example 36 and 2.0 mL of THF were added dropwise and the cooling bath was removed. The resulting solution was stirred at room temperature for 48 hours and 0.25 mL of acetic acid was added. The resulting mixture was diluted with 50 mL of water, 50 mL of dichloromethane and 10 mL of 1M $NaHCO_3$, stirred for 30 minutes and allowed to settle into two phases over a 24 hour period. The precipitate in the aqueous layer was collected by filtration and purified by column chromatography (silica gel; 4:1 $CH_2Cl_2:CH_3CO_2H$ ) to give 0.15 g of the title compound. MS(FAB): 416[M$^+$+1],415[M$^+$].

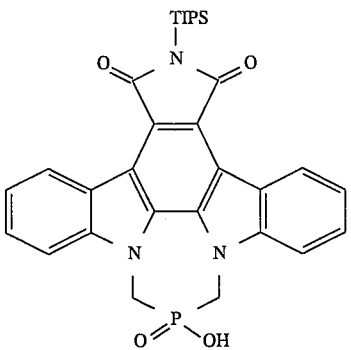

Example 38

2-[Tri(1-methylethyl)silyl]1H,9H,11H-diindolo [1,2-e:2,1-k]-pyrrolo[3,4-h][1,5,3] benzdiazaphosphepine-1,3(2H)-dione 10-oxide This compound was isolated as another component from the chromatography column described in Example 38. It was also present in the $CH_2Cl_2$ extracts and could be isolated by column chromatography (6:1:1, hexane:$CH_2Cl_2$:EtOAc then 4:1 $CH_2Cl_2$:acetone then acetone). The total yield of this component was 0.27 g. MS(FAB):571(36%),528(100%)

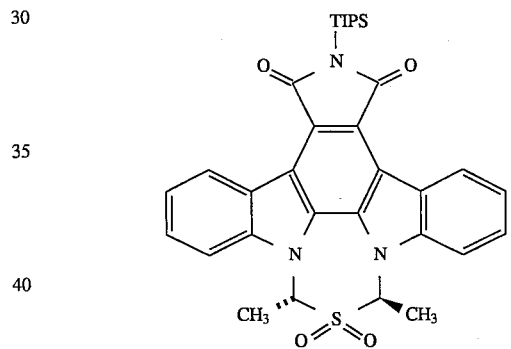

Example 39

REL-(R,R)-Dimethyl-2-triisopropyl silyl-1H,9H,11H-diindolo[1,2,3-et:3',2',1'-jk] pyrrolo-[3,4-h][3,1,5]-benzothiadiazepine- 1,3(2H)-dione 10, 10-dioxide A 50 mL flask was charged with 2.44 mL of a 1.0M solution of $NaN(Si(CH_3))_2$ in tetrahydrofuran (THF) and cooled to −78° C. A solution of 0.70 g of the compound from Example 26 and 17.0 mL of THF was added dropwise and the resulting mixture was stirred for 1.0 hour when 0.35 mL of $CH_3I$ was added. The resulting mixture was stirred for 1.0 hour then warmed to room temperature and stirred for 4 hours. A saturated solution of $NH_4Cl$ was added and the mixture was extracted with dichloromethane. The organic extracts were washed with water, brine, dried over $MgSO_4$, filtered and evaporated to give a crude oil which was purified by column chromatography (silica gel/eluant:hexane:dichloromethane:ethyl acetate, 100:10:1) to give 0.18 g of the title compound.

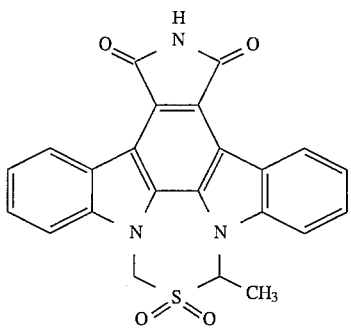

Example 40

9-Methyl-1H,9H,11H-diindolo[1,2,3-ef:3',2',1'-jk]
pyrrolo-[3,4-h][3,1,5]-benzothiadiazepine-
1,3(2H)-dione 10,10-dioxide In a 10 mL flask was placed 0.17 g of the compound from Example 27, 8.0 mL of acetic acid, 2.0 mL of water and 0.10 g of sodium acetate. The resulting mixture was heated at 65° C. for 16 hours, cooled and poured into ice and water. The resulting yellow precipitate was collected, washed with water and dried in vacuo (2.0 mm Hg) for 2 days to give 0.08 g of the title compound.

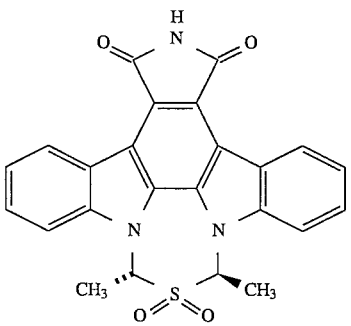

Example 41

REL-(R,R)-9,11-Dimethyl-1H,9H,11H-diindolo
[1,2,3-ef:3',2',1'-jk]pyrrolo-[3,4-h][3,1,5]-
benzothiadiazepine-1,3(2H)-dione 10,10-dioxide The compound from Example 39 (0.18 g) was subjected to the reaction conditions of Example 40, except the mixture was heated at 100° C. The title compound (0.009 g) was collected. decomp. pt.: 280°–282° C.; HRMS: calc'd: 443.0940; measured: 443.0922. As used herein, the term REL means that the stereochemistry given for the above compound is not absolute but rather is the relative stereochemistry.

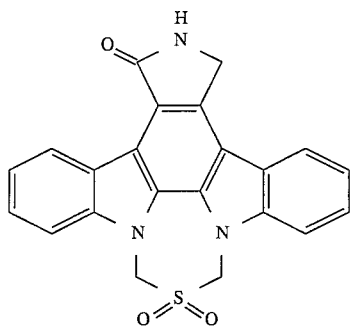

Example 42

2,3-Dihydro-1H,9H,11H-diindol[1,2,3-ef:3',2',1'-jk]-
pyrrolo-[3,4-h][3,1,5]-benzothiadiazepine-
1-one,1-10-dioxide To a mixture of 2.25 g of the compound from Example 20 and 0.83 L of DMF was added 9.58 g of monoperoxyphthalic acid, magnesium salt hexahydrate, portionwise, over a period of 30 minutes. The resulting solution was stirred for 3 hours, cooled in an ice bath and an aqueous solution containing 110 mL of 10% $Na_2SO_3$, 7.5 g of $NaHCO_3$ and 2.47 L of cold water was added dropwise. The precipitate formed was collected by suction filtration, added under nitrogen with suction for 40 minutes and dried in a vacuum oven at room temperature for 18 hours to give 1.91 g of the title compound as a pale yellow solid. MS(FAB): 401(5%), 402(17%); decomp. pt.: 325°–327° C.

The title compound was also prepared in 89% yield starting with the title compound of Example 22 and using the procedure outlined in Example 43 below.

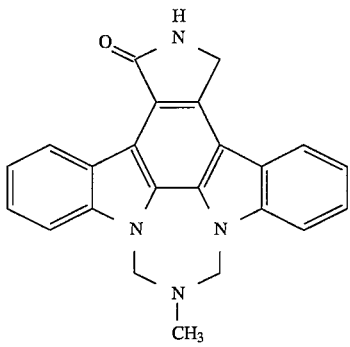

Example 43

10,11-Dihydro-10-methyl-1H,9H,11H-diindolo
[1,2,3-ef:3',2',1'-jk]pyrrolo-[3,4-h][1,3,5]-
benzothiadiazepine-1-one The compound from Example 3 (57 mg) was mixed with 2.0 mL of diglyme and 0.08 mL of boron trifluoride etherate and cooled to 0° C. A solution of 0.024 g of sodium borohydride in 2.0 mL of diglyme was added. The resulting solution was stirred overnight at room temperature, cooled to 0° C. and 20 mL of water was added slowly dropwise. The precipitate was filtered and added in a vacuum oven at 55° C. for 18 hours to give 43 mg of the title compound as a light brown solid. Decomposition point: 230°–232° C. (brown to black); MS(FAB): 351(14%),352(33%),366(88%),367 (100%).

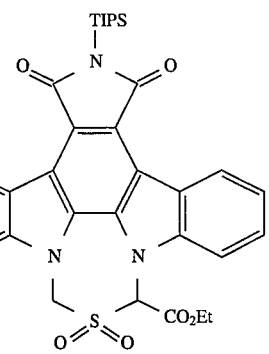

Example 44

Ethyl 2,3-Dihydro-1,3-dioxo-2-triisopropylsily-1H,9H,11H-diindolo[1,2,3-ef:3',2',1'-jk]pyrrolo-[3,4-h][3,1,5]-benzothiadiazepine-9-carboxylate 10,10-dioxide In a 125 mL round bottomed flask were placed 0.05 g of the compound from Example 26 and 50.0 mL of THF and the solution was cooled to −78° C. (bath temperature). A 1.0M solution of Na(NSi(CH$_3$)$_3$)$_2$ in THF was added dropwise (0.86 mL). After stirring for 20 minutes at low temperature, 0.17 mL of ethyl chloroformate was added and the solution was stirred for 1 hour more. Solid NH$_4$Cl was added and the reaction allowed to warm to room temperature. The resulting mixture was partitioned between EtOAc and water and the organic extracts were combined, washed with brine, dried over MgSO4, filtered, evaporated and chromatographed on silica gel, eluting with 2:1 hexanes:dichloromethane to give 0.07 g of the title compound.

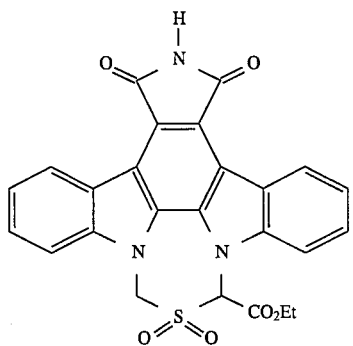

Example 45

Ethyl 2,3-Dihydro-1,3-dioxo-1H,9H,11H-diindolo[1,2,3-ef:3',2',1'-jk]pyrrolo-[3,4-h][3,1,5]-benzothiadiazepine-9-carboxylate 10,10-dioxide In a 10 mL flask were placed 0.07 g of the compound from Example 44, 4.0 mL of dimethyl sulfoxide, 1.0 mL of water and 0.05 g of sodium acetate. The resulting mixture was stirred at room temperature for 16 hours, cooled and poured in to ice and water. The resulting yellow precipitate was collected, washed with water and dried in vacuo (2.0 mm Hg) for 2 days to give 0.04 g of the title compound. mp: 298°–300° C.; HRMS: calc'd: 487.0838; measured: 487.0831

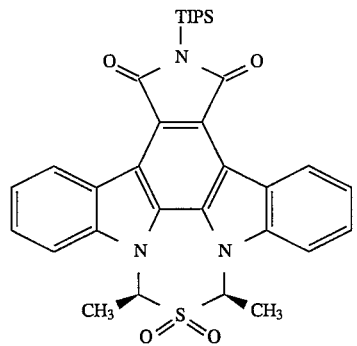

Example 46 meso-Dimethyl-2-triisopropyl silyl-1H,9H,11H-diindolo[1,2,3-ef:3',2',1'-jk] pyrrolo-[3,4-h][3,1,5]-benzothiadiazepine-1,3(2H)-dione 10,10-dioxide The title compound was isolated as another component from the chromatography column described in Example 39. The total yield was 22.0 mg.

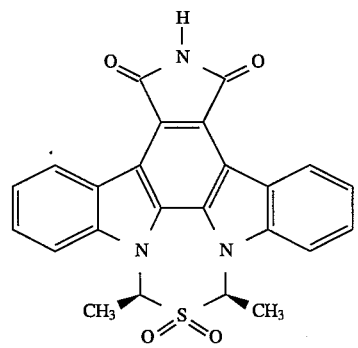

Example 47 meso-9,11-Dimethyl-1H,9H,11H-diindolo [1,2,3-ef:3',2',1'-jk]pyrrolo-[3,4-h][3,1,5]-benzothiadiazepine-1,3(2H)-dione 10,10-dioxide The compound from Example 46 (0.07 g) was subjected to the reaction conditions of Example 40, except the mixture was heated at 100° C. The title compound (11.0 mg) was collected. decomp. pt.: 280°–282° C.; HRMS: calc'd: 443.0940; measured: 443.0947.

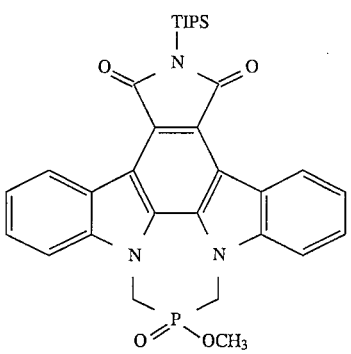

Example 48

2[Tris(1-methyl)silyl]-10-methoxy-
9H,11H-diindolo[1,2,-ef:2,1-k]pyrrolo-[3,4-h]
[3,1,5]-benzothiadiazepine-1,3(2H)-dione
10-dioxide The title compound was present in the $CH_2Cl_2$ extracts described in Example 37 and was isolated from the chromatography column described in Example 38 (less polar component 6:1:1 hexane: $CH_2Cl_2$ EtOAc then 4:1 $CH_2Cl_2$:acetone). The total yield of this component was 0.11 g.

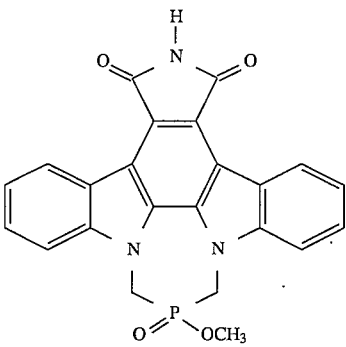

Example 49

10-methoxy-9H,11H-diindolo
[1,2,-ef:2,1-k]pyrrolo-[3,4-h][3,1,5]-
benzodiazaphosephine-1,3(2H)-dione 10-dioxide The compound from example 48 (0.07 g) was dissolved in 8.0 mL of pyridine and 0.10 mL of $HF_x$·pyridine (hydrogen fluoride-pyridine) was added all at once. After stirring for 10 minutes, the reaction solution was poured into ice and water and diluted with $CH_2Cl_2$. The $CH_2Cl_2$ extracts were washed with saturated aqueous $NaHCO_3$, brine, dried over $MgSO_4$, filtered, evaporated and added under vacuum (1.0-mmHg) for 18 hours to give 48 mg of the title compounds as a yellow solid. Decomposition>295° C. (yellow to black); HRMS calc'd 430.0957; measured 430.0948.

For the purpose of understanding the tables below, diindolo rings are reproduced with the appropriate carbons and nitrogens being numbered. It will be understood that in the tables below, the numbering follows the particular ring system of the compound under consideration. For example, in the first table below, the starting materials correspond to the five ring structure which appears below and on the left hand side of the page. Consequently, the numbering in the table of starting materials follows the numbering in this structure. On the other hand, in the first table below, the end products correspond to the seven ring structure which appears in the center of the page. Consequently, the numbering of the end products in this table corresponds to the numbering in this seven ring structure.

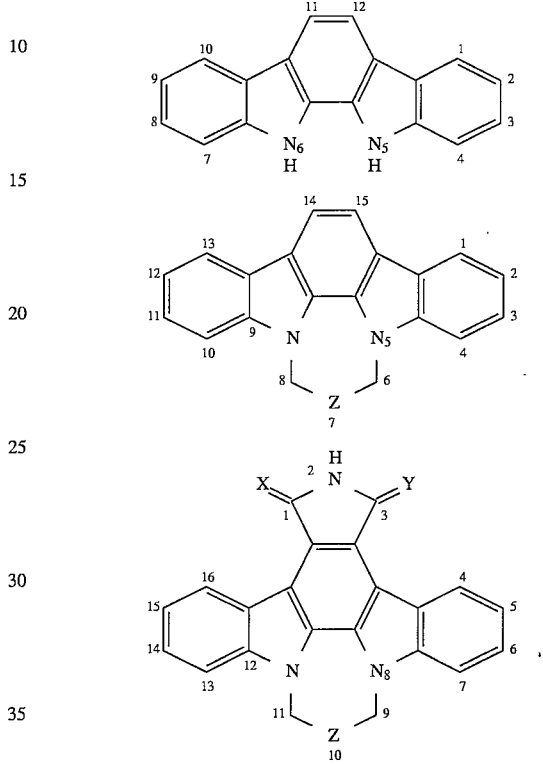

By substituting the following starting materials for 11,12-dicyano indolocarbazole and methyl amine of Example 1 and following the procedures of Examples 1 and 2; Examples 1, 2 and 20 or Examples 1,2,3 and 23,24; Examples 1,2,3 and 23; or Examples 1 through 3, the following end products can be made:

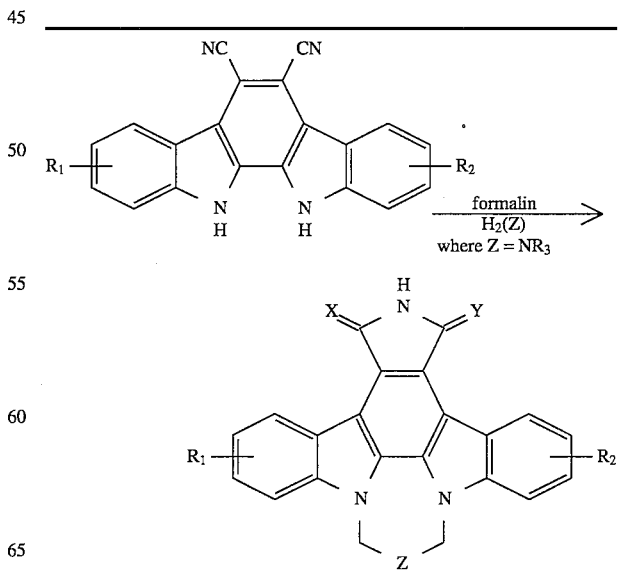

| Starting Material R₁=R₂ | End Products R₁=R₂ | R₃ | X | Y |
|---|---|---|---|---|
| OH: 1,10 or 2,9 or 3,8 or 4,7 | OH: 4,16 or 5,15 or 6,14 or 7, 13 | OH | O | NH |
| OH: 1,10 or 2,9 or 3,8 or 4,7 | OH: 4,16 or 5,15 or 6,14 or 7, 13 | OH | O | H,H |
| OH: 1,10 or 2,9 or 3,8 or 4,7 | OH: 4,16 or 5,15 or 6,14 or 7, 13 | OH | O | H,OH |
| H | H | cyclopropyl | O | H,OH |
| H | H | cyclopropyl | O | O |
| OH: 1,10 or 2,9 or 3,8 or 4,7 | OH: 4,16 or 5,15 or 6,14 or 7, 13 | n-butyl | O | NH |
| OH: 1,10 or 2,9 or 3,8 or 4,7 | OH: 4,16 or 5,15 or 6,14 or 7, 13 | n-butyl | O | H,H |
| OCH₃: 1,10 or 2,9 or 3,8 or 4,7 | OCH₃: 4,16 or 5,15 or 6,14 or 7, 13 | $C_{10}H_{21}$ | O | O |
| CH₃: 1,10 or 2,9 or 3,8 or 4,7 | CH₃: 4,16 or 5,15 or 6,14 or 7, 13 | $C_{10}H_{21}$ | O | NH |
| CH₃: 1,10 or 2,9 or 3,8 or 4,7 | CH₃: 4,16 or 5,15 or 6,14 or 7, 13 | $C_{10}H_{21}$ | O | H,H |
| CH₃: 1,10 or 2,9 or 3,8 or 4,7 | CH₃: 4,16 or 5,15 or 6,14 or 7, 13 | $C_{10}H_{21}$ | O | H,OH |
| CH₃: 1,10 or 2,9 or 3,8 or 4,7 | CH₃: 4,16 or 5,15 or 6,14 or 7, 13 | $C_{10}H_{21}$ | O | O |
| H | H | $C_{10}H_{21}$ | O | NH |
| H | H | $C_{10}H_{21}$ | O | H,H |
| H | H | $C_{10}H_{21}$ | O | H,OH |
| H | H | $C_{10}H_{21}$ | O | O |

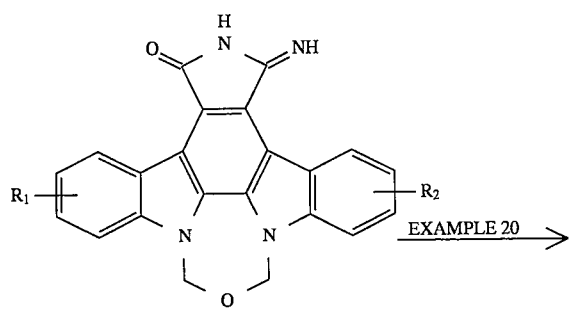

EXAMPLE 20

By substituting the following starting materials for 2,3-dihydro-3-imino-1H,9H,11H-diindolo[1,2,3-ef:3',2',1'-jk}pyrrolo[3,4-h][3,1,5]-benzoxadiazepin-1-one and using the conditions outlined in Example 20, the following end products can be made in a like manner:

| R₁=R₂; Starting Material | R₁=R₂; End Product |
|---|---|
| OCH₃: 4,16- or 5,15- or 6,14- or 7,13- | OCH₃: 4,16- or 5,15- or 6,14- or 7,13- |

By substituting the following starting materials for 1H,9H,11H-diindolo[1,2,3-ef:3',2',1'-jk]pyrrolo[3,4-h][3,1,5]-benzoxadiazepin-1,3(2H)-dione and using the conditions outlined in Example 23, the following end products can be made in a like manner:

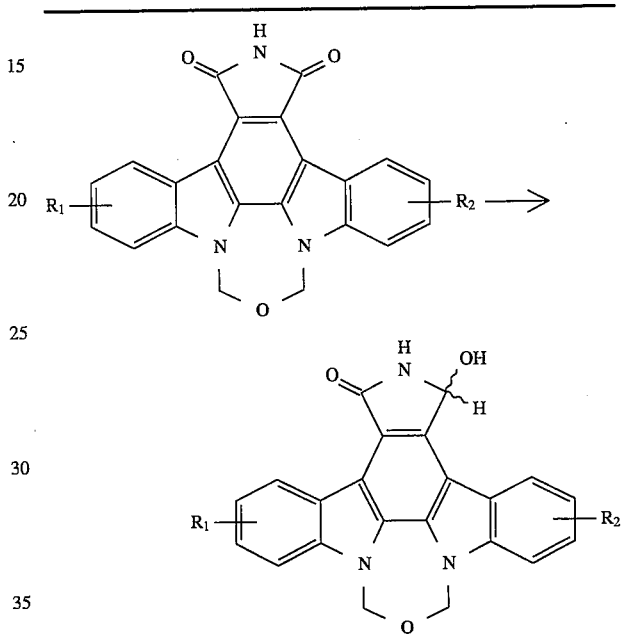

| R₁=R₂; Starting Material | R₁=R₂; End Product |
|---|---|
| Cl: 4,16- or 5,15- or 6,14- or 7,13- | Cl: 4,16- or 5,15- or 6,14- or 7,13- |

By substituting the following starting materials for indolocarbazole and using the conditions outlined in Examples 12,13,6,2 and 3, the following end products can be made in a like manner:

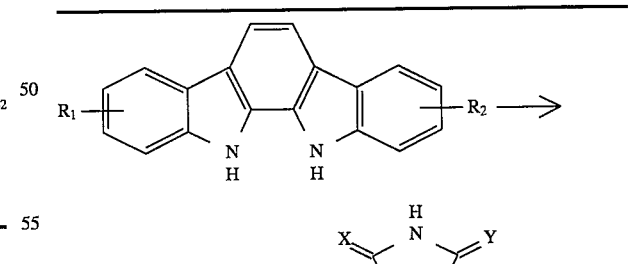

-continued

| Starting Material | End Products | | |
|---|---|---|---|
| $R_1 = R_2$ | $R_1 = R_2$ | X | Y |
| OH: 1,10 or 2,9 or 3,8 or 4,7 | OH: 4,16 or 5,15 or 6,14 or 7, 13 | O | O |

By substituting the following starting materials for 11,12-dicyano indolocarbazole and using the conditions outlined in Examples 17, 2 and 3, the following end products can be made in a like manner:

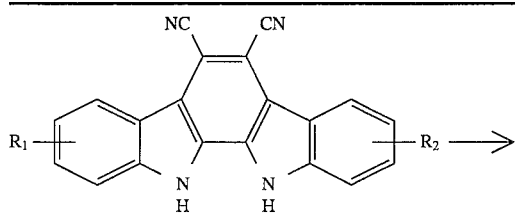

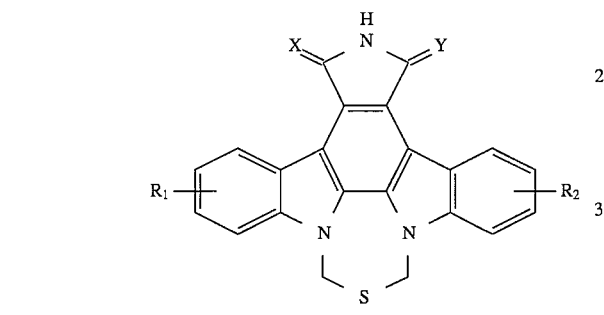

| Starting Material | End Products | | |
|---|---|---|---|
| $R_1 = R_2$ | $R_1 = R_2$ | X | Y |
| OCH$_3$: 1,10 or 2,9 or 3,8 or 4,7 | OCH$_3$: 4,16 or 5,15 or 6,14 or 7, 13 | O | O |

By substituting the following starting materials for 1H,9H,11H-3-Imino-2,3-dihydro-diindolo[1,2,3-ef:3',2',1'-jk]pyrrolo-[3,4-h][3,1,5]-benzothiadiazepine-3-one and using the conditions outlined in Example 20, the following end products can be made in a like manner:

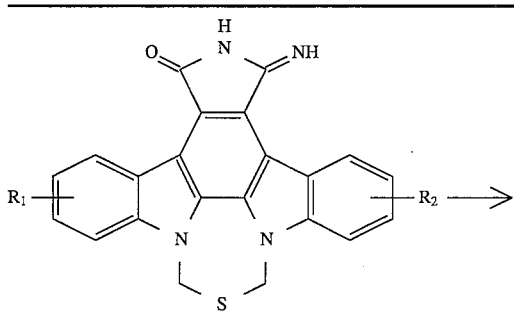

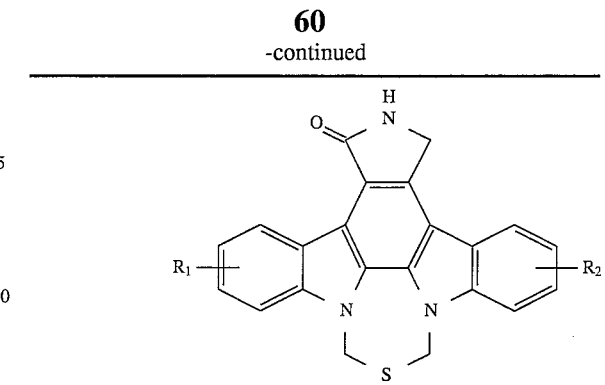

| $R_1 = R_2$; Starting Material | $R_1 = R_2$; End Product |
|---|---|
| Cl: 4,16- or 5,15- or 6,14- or 7,13- | Cl: 4,16- or 5,15- or 6,14- or 7,13- |

By substituting the following starting materials for 1H,9H,11H-Diindolo[1,2,3-ef:3',2',1'-jk]pyrrolo-[3,4-h][3,1,5]-benzothiadiazepine-1,3-(2H)-dione and using the conditions outlined in Example 23, the following end products can be made in a like manner:

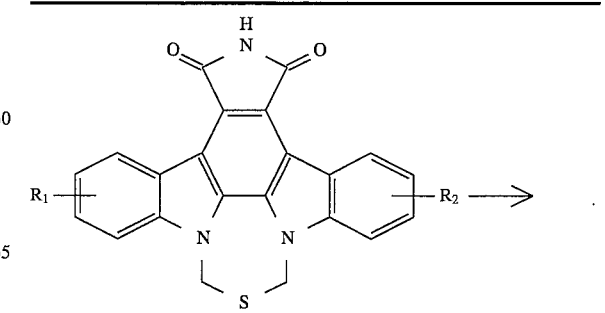

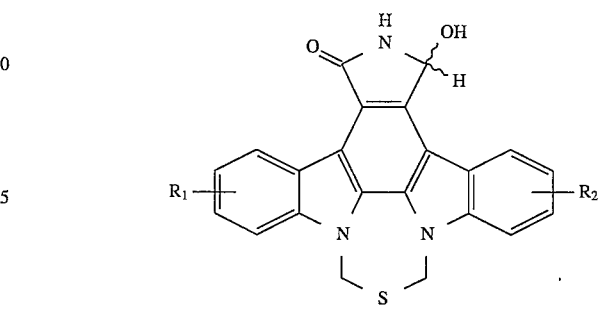

| $R_1 = R_2$; Starting Material | $R_1 = R_2$; End Product |
|---|---|
| F: 4,16- or 5,15- or 6,14- or 7,13- | F: 4,16- or 5,15- or 6,14- or 7,13- |

By substituting the following starting materials for 14,15-dicyano-6H,8H-diindolo[1,2,3-ef:3',2',1'-jk]3,1,5-benzothiazine and using the conditions outlined in Examples 21, 2 and 3 , the following end products can be made in a like manner:

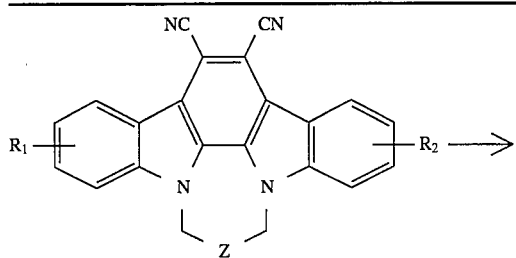

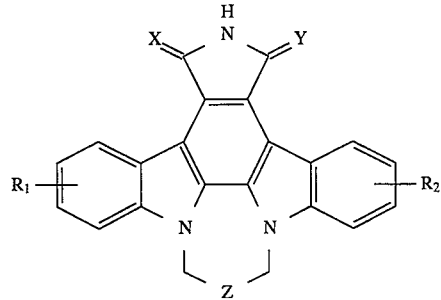

| Starting Materials | | End Products | | | |
|---|---|---|---|---|---|
| $R_1 = R_2$ | Z | $R_1 = R_2$ | Z | X | Y |
| F: 1,13- or 2,12- or 3,11- or 4,10- | S | F: 4,16- or 5,15- or 6,14- or 7,13- | SO | O | O |

By substituting the following starting materials for 1H,9H,11H-10-oxo-diindolo[1,2,3-ef:3',2',1'-jk]pyrrolo-[3,4-h][3,1,5]-benzthiadiazepine-1,3-(2H)-dione and using the conditions outlined in Examples 23 and 24, the following end products can be made in a like manner:

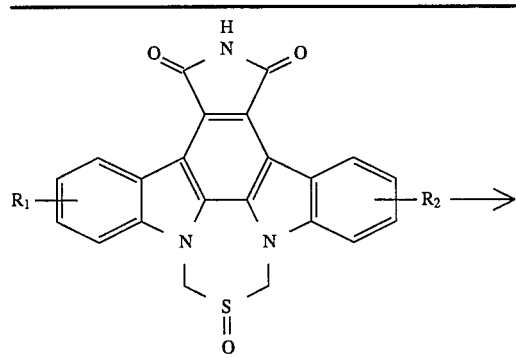

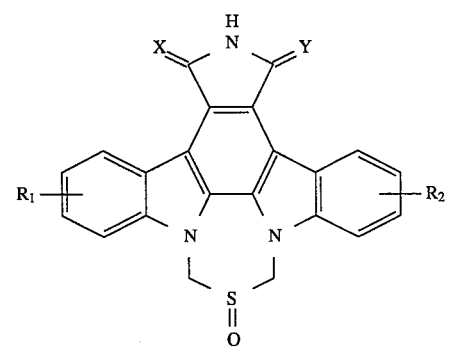

| $R_1 = R_2$ | | X | Y |
|---|---|---|---|
| $OCH_3$: 4,16- or 5,15- or 6,14- or 7,13- | | O | OH,H |
| $OCH_3$: 4,16- or 5,15- or 6,14- or 7,13- | | O | H,H |

By substituting the following starting materials for 14,15-dicyano-6H,8H-diindolo[1,2,3-ef:3',2',1'-jk]3,1,5-benzothiazine and using the conditions outlined in Examples 22, 2 and 3, the following end products can be made in a like manner:

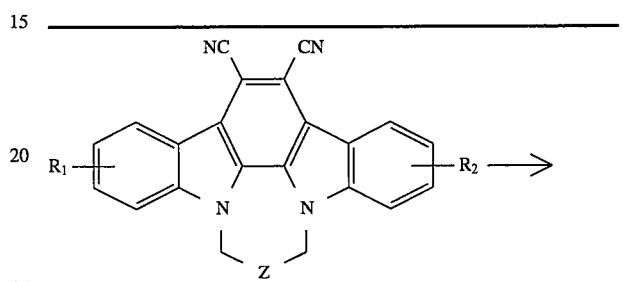

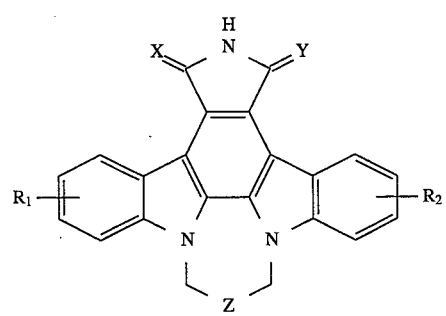

| Starting Materials | | End Products | | | |
|---|---|---|---|---|---|
| $R_1 = R_2$ | Z | $R_1 = R_2$ | Z | X | Y |
| F: 1,13- or 2,12- or 3,11- or 4,10- | S | F: 4,16- or 5,15- or 6,14- or 7,13- | $SO_2$ | O | O |

By substituting the following starting materials for 1H,9H,11H-diindolo[1,2,3-ef:3',2',1'-jk]pyrrolo-[3,4-h][3,1,5]-benzothiadiazepine-1,3(2H)-dione 10,10-dioxide and using the conditions outlined in Example 23 or Examples 23 and 24, the following end products can be made in a like manner:

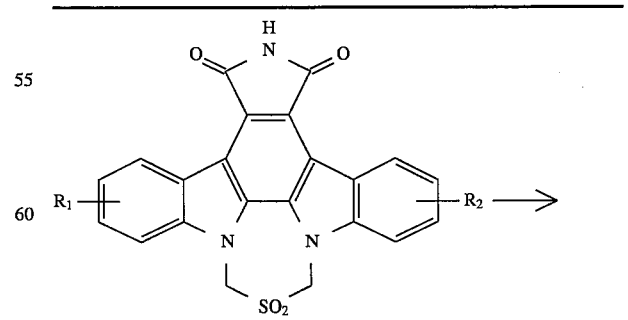

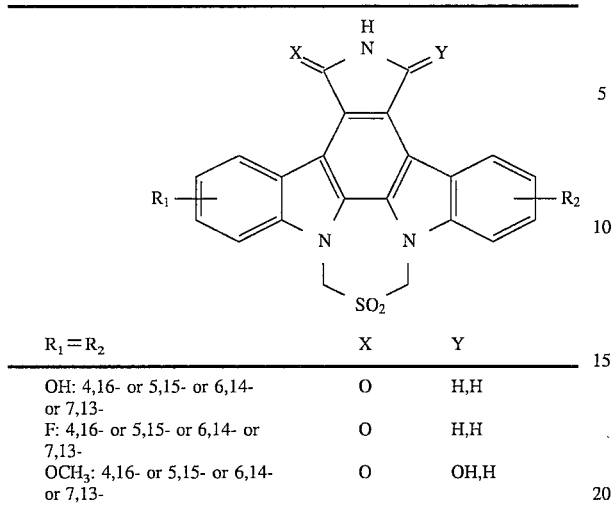

| $R_1 = R_2$ | X | Y |
|---|---|---|
| OH: 4,16- or 5,15- or 6,14- or 7,13- | O | H,H |
| F: 4,16- or 5,15- or 6,14- or 7,13- | O | H,H |
| OCH$_3$: 4,16- or 5,15- or 6,14- or 7,13- | O | OH,H |

By substituting the following starting materials for 2-tri-isopropyl silyl-1H,9H,11H-diindolo[1,2,3-ef:3',2',1'-jk]pyrrolo-[3,4-h][3,1,5]-benzothiadiazepine-1,3(2H)-dione 10,10-dioxide and using the conditions outlined in Examples 30 and 26, the following end products can be made in a like manner:

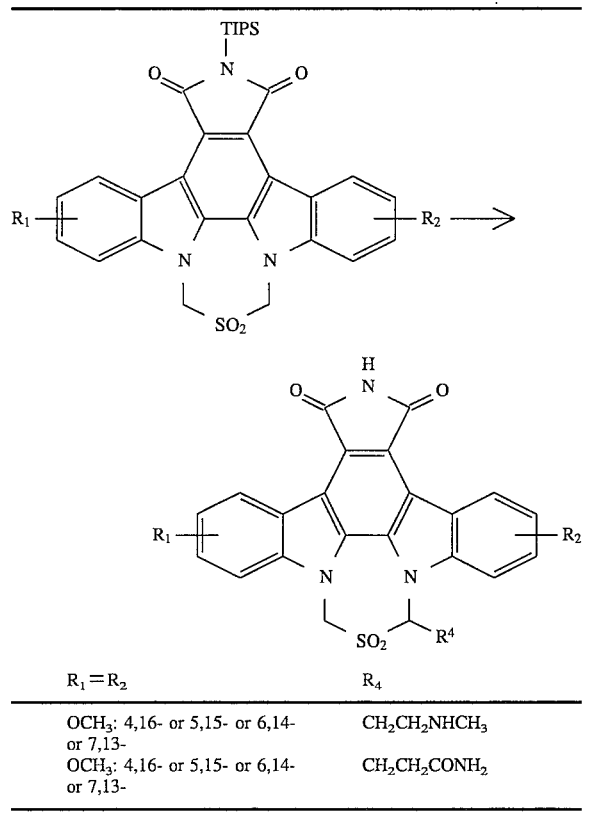

| $R_1 = R_2$ | $R_4$ |
|---|---|
| OCH$_3$: 4,16- or 5,15- or 6,14- or 7,13- | CH$_2$CH$_2$NHCH$_3$ |
| OCH$_3$: 4,16- or 5,15- or 6,14- or 7,13- | CH$_2$CH$_2$CONH$_2$ |

By substituting the following starting materials for 2-tri-isopropyl silyl-1H,9H,11H-diindolo[1,2,3-ef:3',2',1'-jk]pyrrolo-[3,4-h][3,1,5]-benzothiadiazepine-1,3(2H)-dione 10,10-dioxide and using the conditions outlined in Examples 31 and 26, the following end products can be made in a like manner:

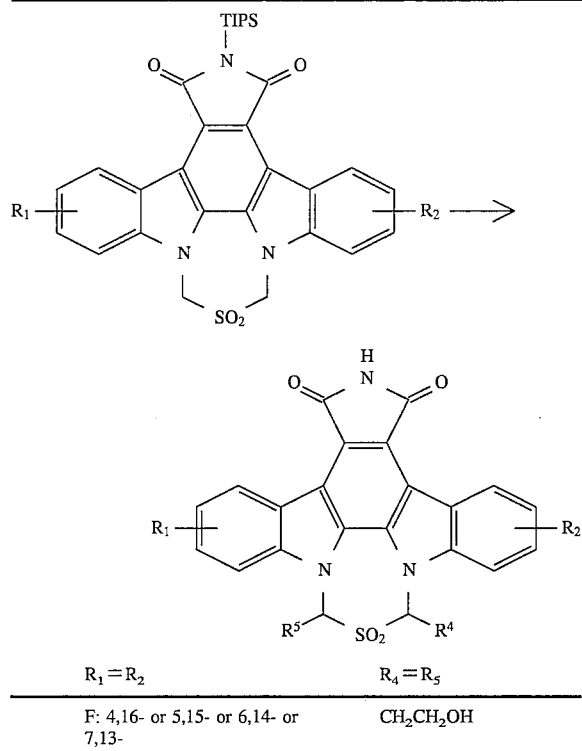

| $R_1 = R_2$ | $R_4 = R_5$ |
|---|---|
| F: 4,16- or 5,15- or 6,14- or 7,13- | CH$_2$CH$_2$OH |

A composition comprising a compound of the invention may be made as follows:

| Number | Ingredient | Concentration (mg/g) |
|---|---|---|
| 1. | Active Ingredient | 10 |
| 2. | Benzyl Alcohol | 10 |
| 3. | Mineral Oil, USP | 30 |
| 4. | White petrolatum | 180 |
| 5. | Stearyl Alcohol | 72 |
| 6. | Ceteth 20 | 22.5 |
| 7. | Sodium Phosphate Monohydrate R | 2.65 |
| 8. | Sodium Phosphate Dibasic Anhydrous R | 0.02 |
| 9. | Sodium Hydroxide NF | * |
| 10. | Phosphoric acid NF | * |
| 11. | Purified Water USP | q.s. |

*Use as a 1% w/v or 10% w/v aqueous solution if needed to adjust the pH to 5.0 ± 0.2. Active ingredient means any compound of formula I of the invention.

1. Mix ingredients 7, 8, 2, and a portion of water at a temperature in the range of 65° to about 75° C.
2. In a separate vessel mix ingredients 4, 3, 5, and a portion of 6 at a temperature in the range of 65° to about 75° C.
3. Add the mixture of step 2 to the mixture of step 1 and mix thoroughly at a temperature in the range of 65° to about 75° C. If needed adjust the pH with a 10% (w/v) aqueous solution of phosphoric acid or sodium hydroxide to 5.1±0.1.
4. Cool the resulting mixture to approximately 40° C.
5. In a separate vessel dissolve the remaining portion of ingredient 6 in a portion of water heated to a temperature in the range of 600° to about 70° C. Cool the resulting mixture to about 40° C.

6. Add ingredient 1 to the mixture of step 5 with agitation.
7. Add the mixture of step 6 and the remaining water to mixture of step 4 mix thoroughly. If needed adjust the pH of the resulting mixture with a 1% (w/v) aqueous solution of phosphoric acid or sodium hydroxide to 5.1±0.2.
8. Cool the cream to room temperature with appropriate agitation.

What is claimed is:

1. A compound of the formula

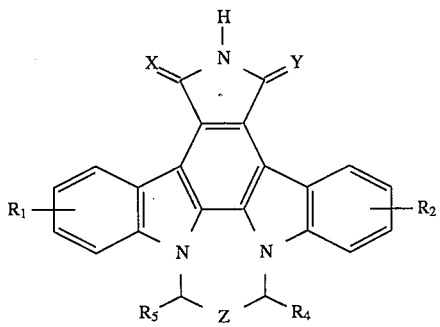

I or pharmaceutically acceptable salts thereof, wherein

X and Y are independently =O, =NH, (H,H) or (H,OH);
$R_1$ and $R_2$, are independently —H, —OH, —Cl, —F, —OCH$_3$, or —CH$_3$;
Z is O, S, SO, or SO$_2$;
n is 1 or 2;
m is 0, 1, 2 or 3;
$R_4$ and $R_5$ are the same or different and each independently is selected from the group consisting of H, —(CH$_2$)$_p$OH, —(CH$_2$)$_q$NH$_2$, —(CH$_2$)$_r$NHCH$_3$, —(CH$_2$)$_s$N(CH$_3$)$_2$, —(CH$_2$)$_t$OCH$_3$, —(CH$_2$)$_u$CO$_2$CH$_3$, —CH$_2$CO$_2$CH$_2$CH$_3$, —CH$_2$CH$_2$CO$_2$CH$_3$, —CH$_2$CH$_2$CO$_2$CH$_2$CH$_3$, —CH$_2$CO$_2$tert-Bu., —CH$_2$CO$_2$tert-Bu., —CH$_2$CH$_2$CO$_2$t Bu., and —(CH$_2$)$_v$CO$_2$H —(CH$_2$)$_w$CONH$_2$;
$R_6$ is —C$_1$-C$_4$ alkyl;
p, q, r, s, t, u, v and w are each independently 1 or 2;
with the proviso that when Z is N—R$_3$, O,

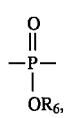

S, or SO, $R_4$ and $R_5$ are both H.

2. A compound according to claim 1, wherein Z is N—R$_3$.
3. A compound according to claim 2, wherein R$_3$ is —(CH$_2$)$_n$CO$_2$H, —(CH$_2$)$_2$OH, —CH$_2$CH$_2$N(CH$_3$)$_2$, —CH$_2$CH$_2$SH, —CH$_2$CH$_2$SCH$_3$, —CH$_2$CO$_2$CH$_3$, —CH$_2$CO$_2$CH$_2$CH$_3$, or —CH$_2$CN.
4. A compound according to claim 2, wherein R$_3$ is —H, —OH or —CH$_3$.
5. A compound according to claim 2, wherein R$_3$ is —CH$_2$CH$_2$N(CH$_3$)$_2$.
6. A compound according to claim 2, wherein X and Y are both O and R$_3$ is —CH$_2$CH$_2$OH.
7. A compound according to claim 1, wherein Z is S, wherein only one of X and Y is O.
8. A compound according to claim 1, wherein Z is SO.
9. A compound according to claim 1, wherein Z is SO$_2$.
10. A compound according to claim 1, wherein Z is O.
11. A compound according to claim 1, wherein X and Y are both O.
12. A compound according to claim 1, wherein R$_1$ and R$_2$ are both H.
13. A compound according to claim 1, wherein Z is SO$_2$ and R$_4$ and R$_5$ are both H.
14. A compound according to claim 1, selected from the group consisting of

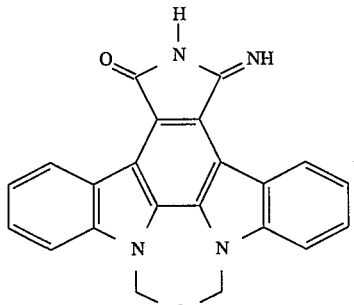

15.

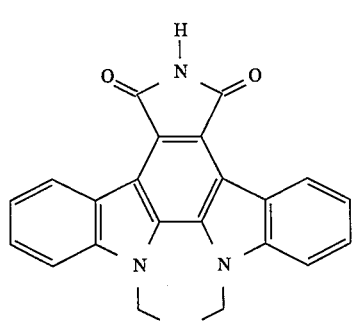

16.

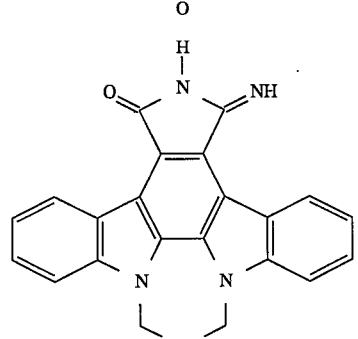

17.

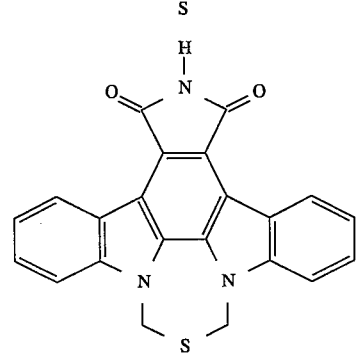

18.

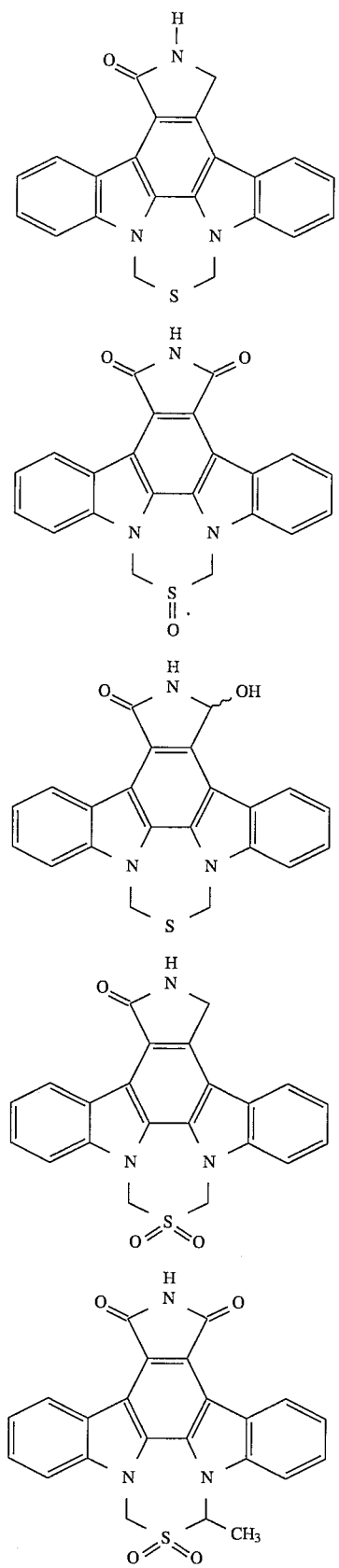

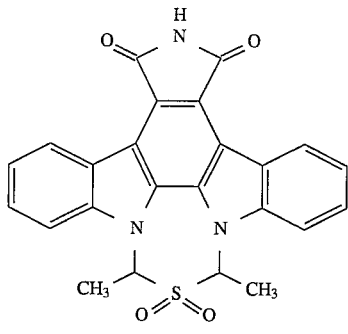

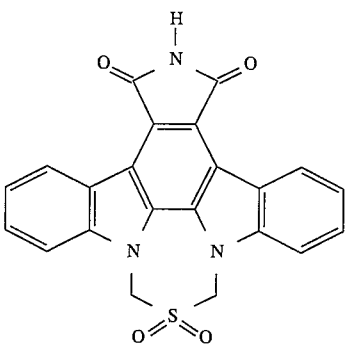

or a pharmaceutically acceptable salt thereof.

15. The compound according to claim 1

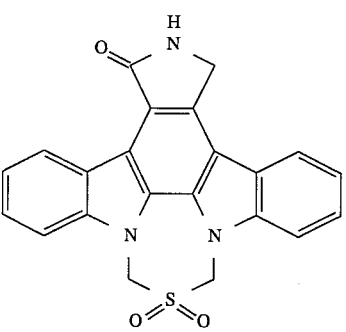

or a pharmaceutically acceptable salt thereof.

16. A pharmaceutical composition comprising a therapeutically effective amount of a compound as defined in claim 1 in combination with a pharmaceutically acceptable carrier.

17. A method for treating a tumor wherein said tumor is treatable by a compound according to claim 1 which inhibits protein kinase C, which comprises administering an antitumor effective amount of said compound to a mammal in need thereof.

* * * * *